United States Patent
Schullian et al.

(10) Patent No.: US 8,045,962 B2
(45) Date of Patent: Oct. 25, 2011

(54) RAILCAR TRANSPORT TELEMATICS SYSTEM

(75) Inventors: John M. Schullian, Tower Lakes, IL (US); David St. Leger-Andrews, San Carlos, CA (US); Christopher J. Weseloh, Mt. Prospect, IL (US)

(73) Assignee: Accenture Global Services Limited, Dublin (IE)

( * ) Notice: Subject to any disclaimer, the term of this patent is extended or adjusted under 35 U.S.C. 154(b) by 1992 days.

(21) Appl. No.: 11/208,039

(22) Filed: Aug. 19, 2005

(65) Prior Publication Data

US 2006/0047379 A1    Mar. 2, 2006

Related U.S. Application Data

(60) Provisional application No. 60/605,218, filed on Aug. 27, 2004, provisional application No. 60/610,368, filed on Sep. 16, 2004.

(51) Int. Cl.
    *G05D 1/00* (2006.01)

(52) U.S. Cl. .......... 455/412.1; 701/19; 701/207; 705/1; 705/25

(58) Field of Classification Search ............... 455/412.1; 701/19, 207; 705/1, 25
    See application file for complete search history.

(56) References Cited

U.S. PATENT DOCUMENTS

| | | | |
|---|---|---|---|
| 5,867,801 A | 2/1999 | Denny | |
| 6,148,291 A * | 11/2000 | Radican | 705/28 |
| 6,236,996 B1 | 5/2001 | Bapat et al. | |
| 6,341,271 B1 * | 1/2002 | Salvo et al. | 705/28 |
| 6,687,609 B2 | 2/2004 | Hsiao et al. | |
| 6,697,735 B2 | 2/2004 | Doyle | |
| 2002/0059075 A1 * | 5/2002 | Schick et al. | 705/1 |
| 2003/0196798 A1 * | 10/2003 | Newman | 166/250.01 |
| 2003/0233189 A1 * | 12/2003 | Hsiao et al. | 701/207 |
| 2004/0138788 A1 | 7/2004 | Herzog et al. | |

FOREIGN PATENT DOCUMENTS

| | | |
|---|---|---|
| CA | 2 322 230 A1 | 10/2000 |
| WO | WO 03/065270 A2 | 8/2003 |
| WO | WO 2004/068160 A2 | 8/2004 |

OTHER PUBLICATIONS

Kurt C. Hoffman, *Real-Time Location Systems Take Asset Tracking To New Level*, Global Logistics & Supply Chain Strategies, pp. 1-5, Oct. 2001.

* cited by examiner

*Primary Examiner* — Charles Appiah
*Assistant Examiner* — William F Rideout
(74) *Attorney, Agent, or Firm* — Fish & Richardson P.C.

(57) ABSTRACT

A railcar asset management system proactively issues an alert or task when a pre-determined event occurs. The system may receive information regarding the location and status of a railcar from sensors on the railcar that may include a telematics sensing unit. A database in the railway telematics system stores the data regarding the railcar location and status information. The system determines whether an event has occurred and issues the proactive alerts and/or task. The system may communicate the proactive alert via e-mail, paging, PDAs or by cell phone and may provide interactive preconfigured web pages.

20 Claims, 14 Drawing Sheets

Figure 6

RAILCAR TRANSPORT TELEMATICS SYSTEM

RELATED APPLICATIONS

This application claims the benefit under §119(e) of U.S. Provisional Application No. 60/605,218, filed Aug. 27, 2004 and U.S. Provisional Application No. 60/610,368, filed Sep. 16, 2004, the entire contents of both of which are incorporated by reference herein.

TECHNICAL FIELD

This invention relates to a Telematics system that tracks the movement, loading and unloading of railcars throughout a rail system.

BACKGROUND

Just-in-time manufacturing is a popular method of controlling inventory costs. Just-in-time manufacturing delivers a product from a product manufacturer to a customer just at the time the customer needs the product. This technique is applied across a wide range of products and can be applied against bulk materials as well as specialty items. These products may be produced at one location and transported to a distant location.

In the case of bulk materials, a shipment is tailored for the most efficient mode of travel, making the use of a railcar or multiple railcars a likely option. A railcar is not only a suitable container for shipment, but the railcar also satisfies the requirement for storage since the railcar approximates the size of a suitable storage vessel capable of holding a vast amount of product. Customers often take delivery of a railcar and hold the railcar on their site for storage purposes, tapping the railcar and removing the product only when required for manufacture.

Such use of railcars causes logistical problems for the product manufacturer. The customer may hold empty or partially empty railcars and return the railcars at the customer's convenience. The product manufacturer will not realize that the railcars are partially empty until the railcars are returned, incurring further costs by taking the railcar off-line for emptying and cleaning when contamination may be an issue. Since the manufacturer must anticipate these situations, the manufacturer will ensure that there are an inflated number of railcars at its disposal resulting in extra capital costs.

Although the railway companies monitor and know the location of the railcars through proprietary systems such as the Lat-Lon® tracking system, there is no affirmative system, for example, that alerts the railway company, the product manufacturer or the customer, that a railcar is sitting in one location for an extended period of time, even when that railcar is empty at a customer's site.

Therefore, a need exists for an integrated Telematics system to provide the information technology to assist in monitoring and managing the railcars to provide an optimum flow of product from the manufacturer to the customer.

BRIEF SUMMARY

The Railcar Telematics System ("System") controls product flow in railcars between a product manufacturer and a customer. The System may identify business events and issue proactive alerts and tasks to affected business users. The users may then resolve any problems and perform any business task that is impeding or delaying the railcar during its roundtrip cycle to the customer and back to the product manufacturer.

In an embodiment, the System may receive transmitted data regarding the railcar weight, indicating the amount of product on the railcar, the product temperature, the ambient temperature surrounding the railcar, the product pressure, the condition of seals on the valves or hatches, and other pertinent information to the customer or manufacturer. The System stores the sensor information or data in a database that may be available to the user.

In a preferred embodiment, the business alert engine processes the sensor information stored in the database for comparison to the metrics of the business rules. The business alert engine optionally supplements the sensor data with information regarding the ordering information and stores the supplemental data in the database as well. The business alert engine then compares the supplemented data against the metrics in the business rules. When a threshold of a metric is exceeded, a proactive alert regarding that metric is issued. Further, a metric for a business rule might indicate a task needs to be performed. This may result from a business event such as the delivery of a railcar to a customer. In such a case, the business alert engine determines that the metric regarding the event has been satisfied and issues a proactive alert or task to a business user or a business enterprise resource planning ("ERP") system. The business user will then take appropriate measures in response.

In one embodiment, the business alert engine may react to data associated representative of a business event, such as idle railcars, by issuing proactive alerts to an individual business user for acknowledgement and resolution of this event. The proactive alert makes the business user aware of an impending event or otherwise issues a task for the user to perform. Once alerted, the user may take action, to resolve the alert or perform the task, increasing the efficient use of the railcar and provide a quality service for both the user and supplier. Further, the system may be configured to report the real-time location and status of a particular railcar or group of railcars without waiting for the system to provide a batch/timed updated status. A batch/timed update may be a railcar information update, such as a status update, that occurs at predetermined times or intervals.

In another embodiment, the business alert engine may generate proactive alerts to the business user. The business user may be the product manufacturer, shipper or the customer. The user may proactively implement any corrective step upon receipt of the alert, ensuring that the railcar and product arrive at the destination on-time. Proactive alerts may be generated because any of the following events or conditions have occurred: the railcar is damaged; the railcar is diverted to another destination; the railcar has been subjected to extreme temperatures; the seal on the railcar is damaged; the railcar has impacted another railcar at an unacceptable speed; the railcar is sitting idle for too long a period; or for any other reason.

In another aspect, the Railcar Telematics System may be tailored to the responsibilities of the individual business user. In one embodiment, a website, configured and tailored to a particular user, is made available to a customer, a customer representative, and others who may be closely associated with a railcar. The business user can include maintenance personnel, railcar schedulers and product manufacturers. Each business user sees the data, metrics, tasks and proactive alerts in views that have a varying level of detail and that may be configured in views tailored to the business user's responsibilities. If the information displayed on the web page does not provide enough detail, the user will be able to drill down on the linked data to obtain more detailed information in another view. For example, the user may first view a summary sheet regarding the round trip of a railcar between the product manufacturer and the customer. The website view may allow the user to link to more specific and detailed information regarding the roundtrip.

BRIEF DESCRIPTION OF THE DRAWINGS

FIG. 6 is a web page view of a Bill of Lading.

DETAILED DESCRIPTION

The elements that are illustrated in the above figures will be explained in more detail in the following discussion. However, it is noted that the following discussion is exemplary and is not limited to the embodiments that are described. For example, although selected aspects, features or components of the implementations are depicted as stored in program, data, or multipurpose system memories, all or parts of the system and methods consistent with the Railcar Telematics System may be stored on or read from other machine-readable media, for example, secondary storage devices such as hard disks, floppy disks, and CD-ROMs; electromagnetic signals; or other forms of machine readable media either currently known or later developed.

Although this specification describes specific components of a Railcar Telematics System, methods, systems and articles of manufacture consistent with the Railcar Telematics System may include additional or different components. For example, a processor may be implemented as a microprocessor, microcontroller, application specific integrated circuit (ASIC), discrete logic, or a combination of other types of circuits acting as explained above. The communication system may be a private data network or a cellular telephone system and may include the Internet or any future communication system that might provide the communications for voice and/or data. The databases, tables, business rules and other data structures may be separately stored and managed, incorporated into a single memory or database, or generally logically and physically organized in many different ways. The programs, such as the proactive business across several memories and processors.

Figure 1:
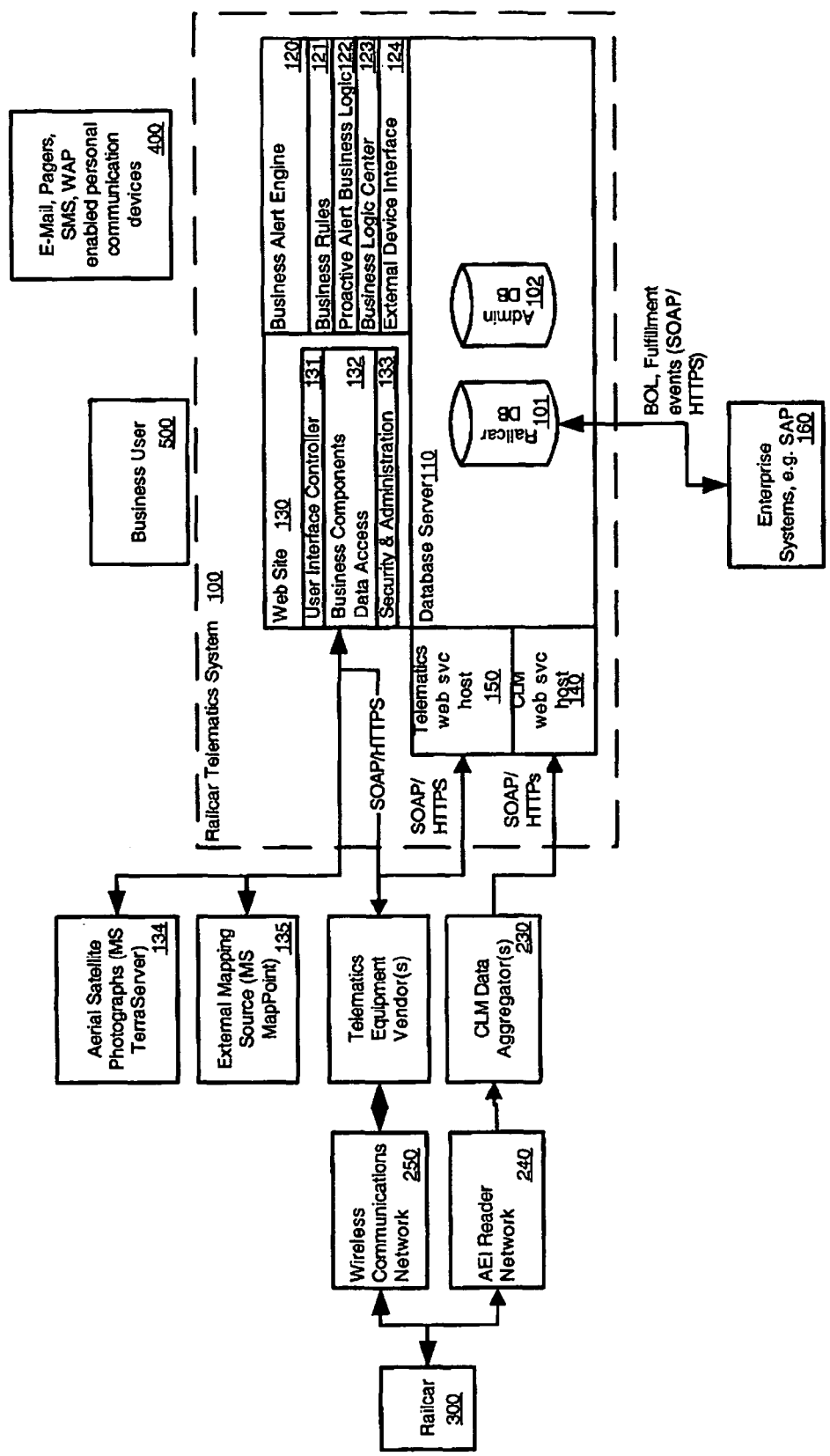
FIG. 1 depicts a block diagram of a Railcar Telematics System.

FIG. 1 is a block diagram a Railcar Telematics System. The Railcar Telematics System 100 may include a database server such as a Microsoft SQL Server 110, or other Relational Database Management System that may include a railcar database 101. The System may also include a Business Alert Engine 120 with executable instructions that configures a data processor in communication with the databases on the Server 110 and communicates information for a business user to a Web Site 130. The Web Site 130 may have access to and overlap either the Arial satellite photographs 210 provided alert engine discussed below may be part of a single program, separate programs, or distributed by a TerraServer® system or an external mapping source 220 provided by a MapPoint® system for displaying the locations of the railcars 300.

The server 110 may communicate unidirectionally or bidirectionally with the railcars using the Railcar Telematics System 100. The Railcar Telematics System 100 will query the railcars 300 through a communication system interface such as a Telematics web service host 150 and a Car Location Message ("CLM") web service host 140. The CLM web service host 140 connects to CLM Data Aggregators 230. The CLM Data Aggregators 230 assemble the data received from an Automatic Equipment Identification Reader Network 240. This network 240 has sensors or readers (not shown) along the railway system that sense or read the information from a radio frequency identification ("RFID") tag (not shown) that is attached to a passing railcar 300.

Figure 2:
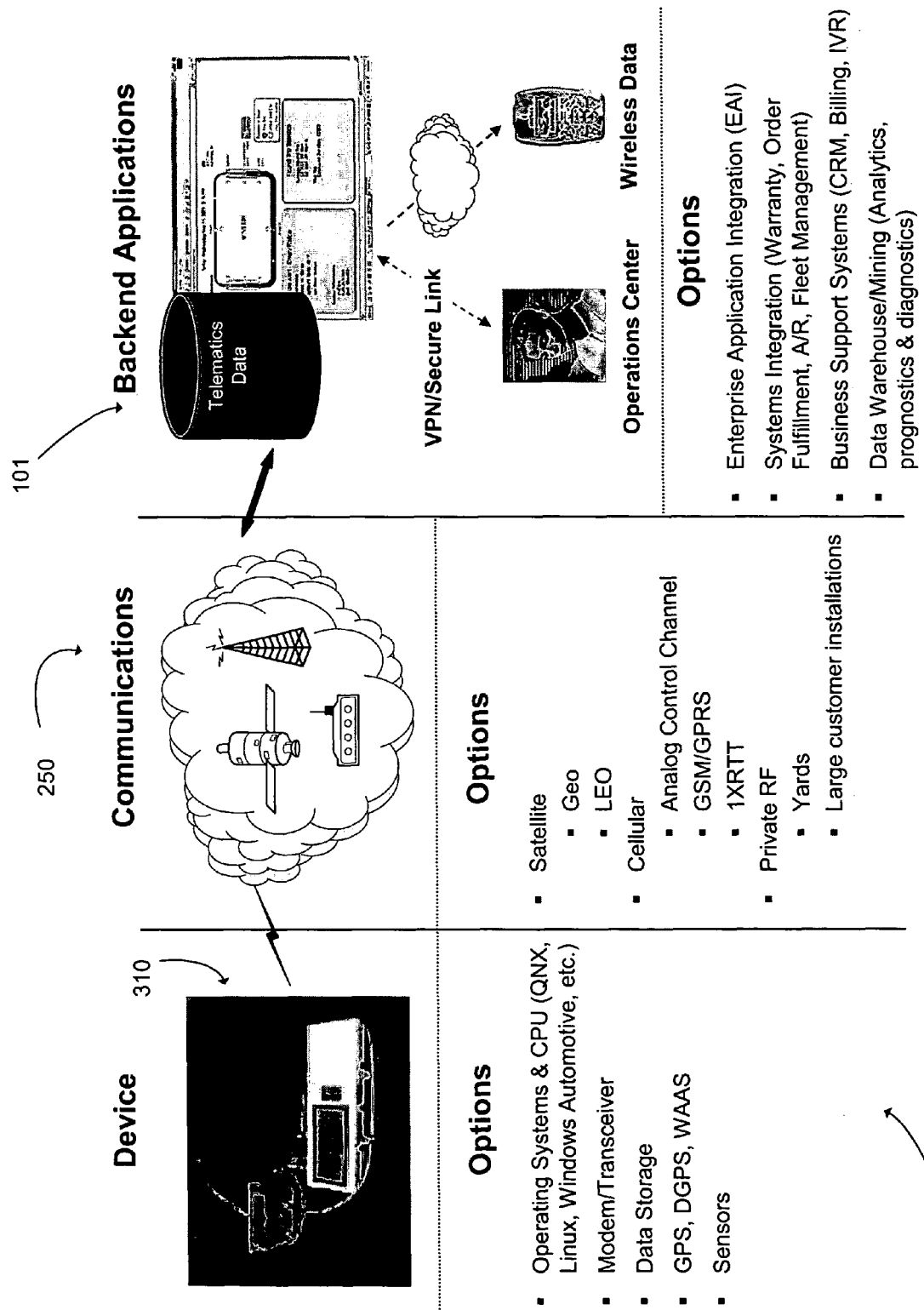
FIG. 2 depicts different communication environments for a Railcar Telematics System.

A Telematics Sensing Unit 310, shown in FIG. 2, may attach to the railcar 300. The Sensing Unit 310 senses different conditions relevant to the state of the railcar 300 and to the product that the railcar 300 contains. FIG. 2 shows optional features of equipment 200 that may be included in the Railcar Telematics System. The optional features of the Telematics Sensing Unit 310 may include data storage, global positioning for determining location and a transceiver unit for communicating the information to the Railcar Telematics System.

Communication options include satellite systems, cellular telephone and private RF network communications. The Telematics System may interface with Enterprise Resource Planning ("ERP systems") thus becoming a part of the Enterprise system. Such a system may interface with Business Support systems for Billing and Inventory Management purposes.

The Railcar Sensor unit 310 may wirelessly transmit sensor information to a Wireless Communication Network 250 as illustrated in FIG. 1. The Network 250 communicates the sensor data, including the status and location of the railcar 300, to a Telematics Equipment Vendor 260. The Vendor 260 may communicate the data to the Telematics Web Service Host 150 within the Railcar Telematics System 100.

The Business Alert Engine 120 may include one or more metrics or sets of metrics that define the Business Rules 121, the Proactive Alert Business Logic 122, the Business Logic Center 123 and the External Device Interface 124. The External Device Interface 124 connects to outside commercial communication systems 400 that will communicate the proactive alerts in voice or text messaging in real-time to the business user 500 or responsible party via paging, cell phones or PDAs.

The Web Site 130 includes a User Interface Controller 131, a Business Components Data Access 132, and Security and Administration Instructions 133. The Business User 500 accesses the Web Site 130 allowing the user to view the portion of the data that has been configured for the business user 500.

The Railcar Telematics System 100 may proactively manage the railcar asset. The business alert engine 120 processes existing data about the status of the product and the location and status of the railcar 300, analyzes the raw data against the product ordering requirements received from the ERP 160 and configures the data into potential business events. The business alert engine 120 may compare or evaluate the events and the information received from the sensors against pre-existing metrics defined in the business rules. If the business alert engine determines an event has occurred from comparison with the metrics, it may issue tasks and/or proactive alerts.

The Railcar Telematics System 100 may receive real-time telemetry data regarding information about the railcar from the mobile Telematics Sensing Unit 310. The telemetry data provides sensor readings that include the location and weight of the railcar, temperature, and impact forces that the railcar endured and any other information that the business user may request or specify. The mobile Telematics Sensor Unit 310 may include a geo-sensing unit for obtaining the location information. The mobile Telematics Sensor Unit 310 communicates the location information and sensor readings through the communications systems 250. The communications system 250 may include a satellite system, a cellular phone system, a private communication system, or other communication system. This location information and the sensor readings are transmitted from the communication system 250 through a Telematics Equipment vendor 260 as shown in FIG. 1 to the Railcar Telematics system 100.

In one implementation, the information may originate from the RFID tag as the railcar 300 passes by a sensor and from the mobile Telematics Unit 310 attached to the railcar 300. The RFID tag provides informational data relating to the identity of the railcar 300 as it passes the RFID readers located along designated points of the railway system. This information is fed through an Automatic Equipment Identifier Reader network and to the database in the Railcar Telematics System. The RFID readers are also known as RFID sensors, and the terms are used interchangeably throughout this specification.

Figure 3:
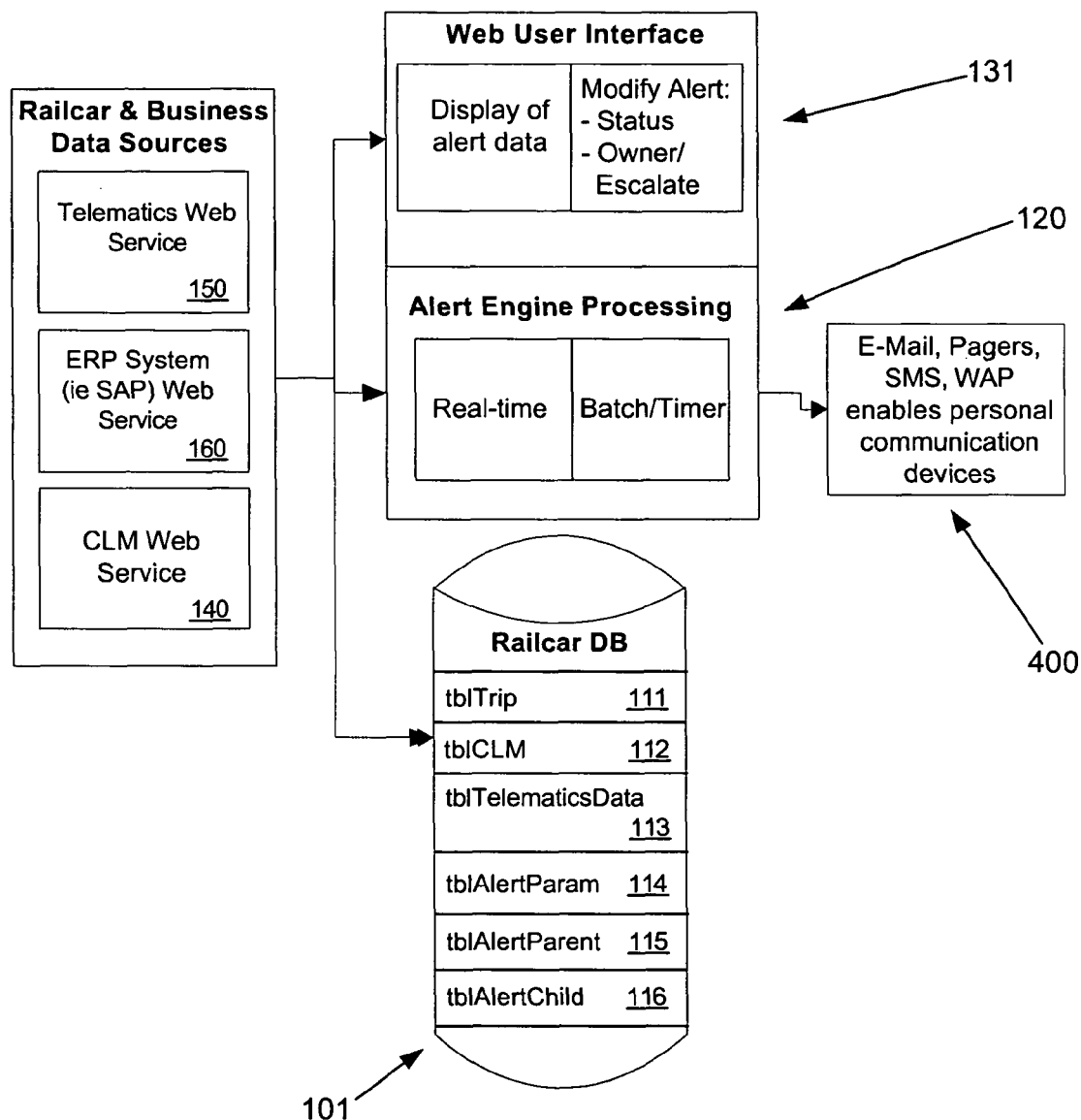
FIG. 3 is a block diagram of another embodiment of the Railcar Telematics System.

In FIG. 3, the CLM 140, the Telematics Web Service 150 and the "ERP System Web Service (i.e. SAP® enterprise business software) 160 communicate data to the Railcar database 101. Tables in the Railcar database 101 may organize the information in the database 101. The tables may include a tblCLM ("CLM Table") 112, a tblTelematicsData ("Telematics Table") 113, a tblTrip ("Trip Table") 111, a tblAlert Param ("Alert Parameter Table") 114, a tblAlertParent ("Parent Alert Table") 115 and a tblAlertChild ("Child Alert Table") 116 table.

The data in the CLM Table 112 includes CLM information received from sensors reading the RFID tags related to the current trip of the railcar 300. Other information in the table may include the estimated time of arrival ("ETA") at the destination as posted by the rail system, the responsible party for the railcar and the date and time each sensor was passed.

The data received from the Telematics sensor unit 310 is stored in the Telematics Table 113. Each message received from the Telematics Sensor unit 310 creates an entry in the Telematics Table 113. Information such as the geo-position, temperature, heading, speed, weight and any impact-related information such as gravitational ("G") forces and the direction of the "G" forces are recorded in the Telematics table 113.

Data regarding the product, including origin, destination, planned time for departure and the actual departure time, may be stored in the Trip Table 111. The data in the Trip table 111 may be general business information regarding the product. The general business information may specify the parameters of the trip, which may be the end-to-end trip cycle of the railcar. As the railcar 300 progresses through the trip cycle, it may incur events. These events may occur at the loading stage at the manufacturer's site, through the transit cycle to the customer site, at the customer site where the railcar 300 is unloaded and upon the trip back to the manufacturer where the railcar 300 may be processed and loaded. Events may include the multiple times that the RFID tags are sensed as the railcar 300 travels to the customer site. The business alert engine 120 may receive, derive, or configure information such as the estimated time of arrival, date for unloading and total trip length. The business alert engine may update the information in the Trip table 111.

The location information data received from the CLM Web service may be stored in the CLM Table 112. The data received from the Telematics Web Service 150 may be stored in the Telematics Table 113. The data regarding the business information received from the ERP System may be stored in the Trip Table 111 in the database 101. The Railcar Telematics system 100 analyzes this data, categorizes it and conditions the data for viewing, for example when the business user so requests. When categorizing, the business alert engine may place the configured data into other tables for further processing and for simplification of the system. The data may be viewed when the business user makes a request through an interactive display.

The business alert engine 120 may be a software module that monitors multiple data streams for business events and trends. In one implementation, the business alert engine utilizing the data processor may analyze or evaluate the discrete telematics sensor data stored in the database 101 to determine business impacting events and related trends and alert the responsible user when the events and trends exceed predetermined threshold values. During a trip, the business alert engine 120 may sense the temperature of a product while the railcar 300 is in transit. The business alert engine may make a historical record of the temperature and locate the data in a historical temperature record. This information will be available to the business user at a later time if needed.

In an alternative implementation, the business alert engine 120 may use the historical record for any sensor to establish a business impact trend. If a trend is established, the business alert engine 120 notifies the responsible party or user of the severity of the trend. The business alert engine may use a pre-determined method for communicating the proactive alert via e-mail, paging or phone.

The alert engine 120 operates in two processing modes. The first mode is a real-time mode and the second mode is a batch/timed mode. In the real-time mode, as information or events are received from the railcar, the data is stored in the database as raw data. The business alert engine 120 may categorize the data based upon the business information in the Trip table 111. The business alert engine may compare or associate the raw data and the categorized data to the metrics of the business rules to determine if a business impacting event exists. If the association or comparison determines that a business impacting event exists, then the business alert engine 120 issues a proactive alert or task. For example, if the temperature of a product has reached or exceeded a threshold, either a high or low temperature, then the business alert engine 120 may issue a proactive alert for the elevated or reduced temperature.

In the batch/timed process, the business alert engine 120 will compare selected data to the metrics of the business rules at a particular time. The batch process may execute at one or more pre-selected times and/or dates, regular intervals and/or irregular intervals, or according to any other schedule. For instance, in the preceding temperature example, the alert in a parent alert table and a child alert table, both to be discussed later, may be checked at a pre-configured time to determine if the alert has been acknowledged or resolved. If not, the alert engine will update the proactive alert. If no one has acknowledged or resolved the alert after several or some pre-determined number of batch cycles, the business alert engine 120 may continue to escalate the proactive alert to other business users until all responsible users have been notified.

The alert thresholds may be stored in the database 101, and in one embodiment, they are stored in the Parameter Alert table 114 as shown in FIG. 3. In the Real-time processing mode, the business alert engine 120 analyzes individual messages from the Telematics Sensing Units 310 and the data is compared to the alert thresholds in the Parameter Alert table 114. Some sensor data, such as temperature, may cause a real-time proactive alert to be issued.

In one embodiment, a business event such as a railcar with an RFID tag read by a RFID sensor may give rise to the issuance of a proactive alert and/or task requiring the appropriate business user to respond by performing some function such as issuing an invoice. The location of the RFID sensor may designate a geo-boundary, a geographical location that when the railcar passes that particular sensor, constitutes an entry onto the customer's site. In another embodiment, the same business event, rather than alerting a business user to prepare and send an invoice after a railcar has passed the sensor, may send the invoice, or direct an ERP System to send the invoice directly to the customer. Alternatively, this task may be issued in the batch/timed process rather than a real-time process. In addition, the business alert engine 120 may determine that the sensor was crossed by comparing the raw data that relates the trip information and determine that a boundary was crossed. Once the boundary is crossed, the business alert engine 120 may send an invoice.

In another embodiment, the invoice may be sent after the railcar was tapped rather than passing a sensor bordering the customer's property. This technique may be lucrative for either the customer or the product manufacturer where the agreement between them is for a spot price of the product rather than a contractual term price. If the price rises, then the manufacturer receives more money for the product when the customer taps the railcar. The sensors may determine the time when the railcar was tapped. If the price should drop, it is to the benefit of the customer.

When the business alert engine issues a proactive alert as a result of a specific sensor reading or business impact event, it may create a Parent Alert Table, for example, the tblParentAlert 115 in FIG. 3. The Parent Alert Table 115 may contain the information regarding the specific alert and a record of the status, whether the alert has been acknowledged or resolved. The Parent Alert Table 115 may also include the asset identification, the type and severity of the alert, the date and time the alert occurred, and the responsible party to be contacted.

A second table, known as the Child Alert Table 116, may also be created as shown by tblChildAlert 116 in FIG. 3. The Child Alert Table 116 includes the specific contents of the alert such as the value of the threshold parameter or the sensor reading at the time of the alert. It includes the role of the user or responsible party who receives the proactive alert and it contains the date and time stamp of the alert. In some cases, when the alert has been issued as a result of a batch process, to be discussed further, the Child Alert Table 116 will contain the subsequent date and time stamps and the value of the sensor at that particular time.

The business alert engine 120 may continually issue alerts due to the non-responsiveness of the business user(s) who were sent the initial alert. For example, when the business alert engine 120, during the batch/timed process, determines that a previously issued alert was not resolved or acknowledged, the business alert engine 120 may create a subsequent entry in the Child Alert Table 116 indicating the fact that there has been no response. A subsequent entry in the Child Alert Table may be an additional row containing the updated information concerning the alert. Should the business alert engine continue to determine a lack of acknowledgement or resolution as the batched/timed process cycles, the subsequent entries will eventually include another user or responsible party to be notified. The new responsible party may be a supervisor of the original business user. The escalation of the alert process may continue until either the alert is acknowledge and/or resolved or until all responsible users have been notified. During this time, the original alert is still valid, but it is the new piece of data subsequently entered into the Child Alert Table 116, the non-responsiveness to the previous alerts, that triggers the follow-on alerts.

In another example, after a proactive alert has issued, a condition may have worsened and another threshold may have been exceeded. In the high temperature example above, the Parent Alert Table 115 and the Child Alert Table 116 were issued. If the temperature continues to rise, then the sensor reading may match or exceed the next threshold level stored in the Alert Parameter Table 114. At that time, a subsequent entry will be issued by the business alert engine 120 by entering a row into the Child Alert Table 116 containing the specifics of the alert. This proactive alert is issued during a real-time process.

By way of example, if the first responsible party does not respond, a subsequent entry is made in the Child Alert Table 116 and the proactive alert issues to another responsible party, preferably to the first responsible party's supervisor or co-worker. The process of creating the subsequent entry may be the addition of a row with the inclusion of the new responsible party and the reason for the new proactive alert.

The new proactive alert may be further monitored by the batch process. If no acknowledgement or resolution is registered in the Parent Alert Table 115 for this alert at the pre-determined time, a subsequent entry will be made in the Child Alert Table 116 as another proactive alert is issued. If there continues to be no response, the alert status will once again escalate as before. The responsible party contacted will escalate as well as the severity of the alert.

When the proactive alert is acknowledged or resolved, the status of the Child Alert Tables 116 that are issued to the multiple business users changes. When one user or responsible party resolves the alert, the resolved status may be set to "True" for all of the alerts associated with that Parent Alert Table 115. All of the users who received the alert will see the updated status.

Further, a user does not have to resolve the alert in order for the alert to be resolved. The condition that was responsible for the alert may have corrected itself, may have been corrected by a third party, or may have been resolved in other manners or by other parties. The sensor responsible for the original alert may now be at an acceptable level, meaning that the threshold in the Alert Parameter Table 114 is no longer exceeded or violated. In other words, the sensor has resolved the condition and acknowledged the alert. By way of example, the elevated temperature of the product in the railcar may have dropped below the threshold with no need for the user to take any action.

In another example, the alert may be acknowledged but it is not resolved. For example, no action has been taken to resolve the alert condition for some period of time after an acknowledgement was made. The lack of the action, or resolving, drives the batch process of the business alert engine 120 to issue a subsequent entry in the Child Alert Table 116. Again, the subsequent alert levels may be escalated both in severity and in the level of responsible party notified until all the users have been notified or until the alert has been resolved.

Other information that may be matched to the sensor data in the proactive alert messages are the upper/lower level thresholds and the responsible party such as the Plant, Sales, Safety, Customer Representative, etc. Also, the alert may be associated with a home base or plant and a product type. The method of the alert delivery mechanism may also be defined for the particular alert such as notifying the responsible party via paging, e-mail or telephone call. Also, when the user logs into the configured web page, he may be notified of the proactive alert.

By way of example, when a temperature exceeds 200 degrees F. for Product B, the telemetry unit will send the data information via the Telematics Sensor unit 310. The message may include such information as the GPS, weight and tank temperature. The business alert engine 120 reads the telemetry message, and since excessive temperature was not previously a concern, the business alert engine 120 will consider each data value as a potential alert and will store all of the potential alerts in the database 101. The temperature value is compared against both a lower and upper threshold boundary in the Alert Parameter table 114. In our example, 200 degrees F. is a recognized alert threshold, so there is a match. Other information may be matched before the alert is confirmed and issued such as the role of the business user to be notified and the product type.

The temperature may drop on the next reading, resolving the alert before anyone takes action. However, there is a potential that the temperature may rise once again, dropping below the alert threshold value on the very next reading. The repetitive nature of the event may be relevant to the shipper, customer or product manufacturer. This repetitive event may be monitored by thresholds in the Alert Parameter table 114. If the alert reaches a particular value of repetitiveness and the metric is matched, a proactive alert will be issued for a repetitive alert in the same procedure as described earlier.

At any time, a user may assign the responsibilities for an alert to another user. When an alert becomes active, the action will cause a new Child Alert Table 116 to be generated for the assigned user. The user may re-assign this responsibility by selecting a graphical icon marked, by way of example, a "Reassign Alert" icon (not shown) in the graphical interface of the web user interface 131.

Further, some alerts may have little significance for a given time frame or the system may be burdened with alerts that have a low priority when compared to an ongoing major issue. In that case, a super-user may cancel those alerts that are deemed inappropriate for the given set of circumstances. Alternatively, the super-user may implement a change to the metric of the business rules so that the number of proactive alerts corresponding to that metric is reduced. In some cases, the business rules may implement a change to the metric when a successful response to the proactive alert is achieved. This process may require the approval from the super-user before the implementation is processed.

There are a various number of alerts that the Alert Parameter table 114 will monitor. A sampling of these alerts is listed in Table 1 with a brief description of the alert. Some of the alerts may be sensor-related indicating the status of the product or the railcar 300. Many other alerts are business impact events, thus driving the system to control and manage the use of the assets to maximize delivery of the product. The list may contain any number of proactive alerts in an implementation and the listing is not exhaustive by any means. It is dependent upon a number of factors such as the business unit, the fleet, the product type, the customer, and the site.

TABLE 1

Typical System Alerts

| | | |
|---|---|---|
| 1 | Alert of Idle Car | Through the application business rule capability, users are notified immediately of car idle times outside of the maximum tolerance. With appropriate action, this reduces trip delays, as well as opportunity to reduce demurrage charges. |
| 2 | Alert on Placement | Create system-generated alerts notifying users of car placement at the site (plant/customer/terminal/storage). These alerts can be based on both CLM event placement codes and/or configured geo-fence parameters. |
| 3 | Alert on Sensors outside threshold (incl. Derailment) | Create system-generated alerts on sensor readings outside of business-defined thresholds. These alerts can be routed to specific users based on their role or customized preferences (including Emergency response personnel for derailments). |
| 4 | Alert on Misrouted Cars | Create system-generated alerts notifying users of misrouted cars. Initially, the application will generate these alerts based on comparison to the BOL versus customer geo-fence and the ETA. Once the system captures route history for multiple trips, business rule capability is used to determine a misroute before the railcar ventures too far from the customer site. Additionally, misroute status information can be received as a location update from RoadRunner ™. |
| 5 | Alert on multiple taps | Create system-generated alerts on multiple unload sensor readings on cars with the same product grade/type inside a terminal geo-fence. These alerts can be routed to specific terminal coordinators and helps them enforce the FIFO policy within terminals. |
| 6 | Alert on Anticipated Late Arrivals | Create system-generated alerts for users, including Customers, Terminal Coordinators and Customer representatives, when a specific railcar's ETA occurs after the SAP order's requested delivery date. |
| 7 | Alert on leaking/ vandalized cars | Create system-generated alerts on unload sensor readings outside of a specified geo-fence. These alerts inform Health & Safety users that are interested in real-time notification of significant car weight loss during the in-transit portion of the trip. This could be an indication of a leak or vandalism. |
| 8 | Alert on Inventory Events | Create system-generated alerts when target product inventory levels within a customer or terminal geo-fence reach either the minimum or maximum thresholds. |
| 9 | Alert on Bad Ordered Cars | Create system-generated alerts for notifying the users of bad-ordered cars. This information may allow users to divert another loaded car to the customer alleviating a possible disruption in product delivery. |
| 10 | Alert on Geographic Areas | Create system-generated alerts notifying a user when a car enters or leaves a specific geographic area. This provides the capability to monitor and proactively manage the movements of specific cars. |
| 11 | Alert on Flagged Car Returning | The application alerts site users when a car is inbound to their site that has been flagged for inspection (flag is part of car status). |
| 12 | Alert on Response to Note/Comment | After a user assigns a note/comment to another user for follow-up and that user has responded, the first user will receive notification. This will save time spent in checking for a response until a response has been given. |

Equally important are the proactive alerts that are issued when trends are developing. By way of example, a customer may suddenly increase the number of days to unload a product from a railcar. Or in another example, the customer begins to regularly return a heel of product in the railcar or greater amounts of a heel are present more often than the historical data indicates. Any trend that takes away from or detracts from a constant improvement in the use of the railcar can be monitored by placing the appropriate threshold metric in the Parameter Alert Table 114. Upon comparison to the historical data, a proactive alert may be issued should a trend be established by either the real-time or batch/timed process of the business alert engine 120.

In one embodiment, it may be desirable to predict an Estimated Time of Arrival ("ETA") for any of the railcars 300 that may be in the railway system. The ETA is desirable not only for those railcars 300 routed to a customer but for those railcars 300 that are returning to the product manufacturer. The ETA is derived from historical data based on the same trip or from the CLM data issued by the railroad and the ETA is routinely updated by the business alert engine 120. The ETA is analyzed by the business alert engine 120 to determine the proper timing for shipping subsequent railcars 300 to the customer.

In an implementation, the business alert engine may obtain the ETA data from the CLM table 112 and compare the ETA to the delivery date required by the customer and stored in the Trip table 111. If the ETA extends beyond the delivery date, a proactive alert may issue in the manner described earlier. The criticality of the proactive alert may continually escalate as the lack of delivery approaches a critical stage.

Information in the CLM Table 112 establishes the position of the railcar 300. The information is received from RFID sensors along the railway that sense the RFID tag on the railcar. The location of some of the RFID sensors may mark a boundary that establishes a geo-reference or geo-fence. When the railcar has passed the sensor referencing a geo-fence, the business alert engine 120 will take notice when the information is communicated.

If the Telematics Monitoring Sensor 310 has a GPS system, the embedded computer may be able to calculate the location with respect to the geo-boundaries. The Sensor 310 may transmit the passing of the latitude/longitude position to the System 101 where the event will be stored in the Telematics Table 113. The business alert engine 120 will note the event and transmit the proactive alert/task. Alternatively, the Sensor 310 may transmit only the present coordinates defining the position of the railcar 300. The business alert engine 120 will calculate the location and compare that location to the geo-boundaries stored in the Trip Table 111. When the system evaluates the present location against the geo-boundary and finds a match, the business alert engine may then issue the proactive alert/task.

A geo-boundary may be defined by a series of known sensors such as those RFID sensors surrounding a customer site. Likewise, a geo-path is a string of sensors along a railway path to a particular destination. The locations of these predefined sensors or latitude/longitude coordinates are stored in the System, preferably the Trip Table 111.

In one implementation, the Business Alert engine 120 may apply business rules to the load sensor readings from the railcar 300 to determine the railcar unload or tapped status. If the customer participates in a vendor inventory management ("VIM") program, the vendor or product manufacturer will depend on the sensors for inventory management. The sensor information may be fed to an electronic VIM system, if available, as part of an on-site inventory monitoring capability. The VIM is an inventory control system that monitors the inventory levels at a customer. When inventory levels drop to a certain point, the vendor will order more product. A VIM system relieves the customer of that responsibility. A VIM system reduces the manpower that is required to go out and check each of the railcars 300 for inventory purposes. The VIM system may be tied into or be a part of an ERP system and/or the Railcar Telematics system.

In monitoring the inventory, the user has access to data that indicates the number of times the customer taps the railcar. Coupled with the constant monitoring of the weight, the customer service representative has access to determine where the inventory of the product resides including the railcars 300 that are returning to the product manufacturer's site. The tapped status may also be determined by comparing the current weight of the railcar 300 with the past weight.

By way of example, a railcar 300 may have 25% of the product remaining on board. If this product were being returned to the product manufacturer, the manufacturer might consider this amount, the heel of the product. The manufacturer may also consider the heel waste product. The business rules may have a metric that would cause a proactive alert to issue when a large amount of heel is contained on the railcar 300. Further, if the weight of the railcar were steadily decreasing as the customer unloaded and then for no apparent reason increased, the business alert engine 120 may issue a proactive alert indicating to the product manufacturer that a possible contamination of the railcar occurred.

By monitoring the location of the railcars and the amount of product that is carried and/or stored in the railcars 300, a real-time picture of the inventory assets will be available to the business users. The Business Alert Engine 120 may apply this information against the business rules to control and manage the assets in a cost effective manner. The railcar telematics system will monitor product usage by the customer in order to time future deliveries and to adjust the product manufacturer's assets accordingly.

Historically, much of the information regarding the product and its usage was provided by the customer and the reliability of the information could be questioned. For example, a product may be delivered on consignment and the market price is determined on a daily basis. The price of the material may depend upon the market forces at the time the customer tapped into the railcar 300 to withdraw the product. Knowing the exact time may be crucial for billing purposes and sending an accurate bill. Sensors on the valves or hatches of the railcars 300 may indicate the time that the tapping of the railcar 300 occurred and establish a proper time.

Account managers and Terminal Coordinators are provided access to the amount of product inventory and the location and status of the railcars under their control. The Business Alert Engine 120 assembles the data in real-time and configures the data into a view for the particular business user. For example, an account manager or terminal coordinator would only see the views for the product that impacts their operation.

The same is true for a customer. The customer will only see the information for the railcars that are transporting the product that the customer ordered. All other data regarding the shipments not affecting the customer will not be provided.

The Business managers may have key metrics or Key Performance Indicators ("KPI") by which they measure the efficiency of a business. These are the KPIs that drive performance and profitability. They may include: railcar turns, on-time deliveries, inventory levels, on-site/in-transit car ratios and other important parameters that drive profitability and customer satisfaction.

A listing of some of the information provided by the Railcar Telematics System is shown in Table 2. This information includes the function that will be provided by the system as well as an explanation of those functions. This listing is not all encompassing, but may be tailored to the specific application of a customer, a product, a manufacturer, or a transportation system providing the business user with the elements that may be most important to their application.

TABLE 2

Applications of The Railcar Telematics System

| # | Name | Description |
|---|---|---|
| 1 | Notify Car Unload | The application uses the telematics load sensor readings or electronic seal readings, along with corresponding business rules to determine car unload or tapped status at a vendor managed inventory (VMI) customer location. This is information is provided to the ERP system as part of the on-site inventory monitoring capability. |
| 2 | Receive CLM Information | The application receives event-based CLM data from a third party CLM aggregator to supplement the telematics location information. The CLM data provides input on railroad activity, as well as railroad ownership of the car at any point in time (with the exception of customer/terminal/plant sites). |
| 3 | Notify Car Load | The application uses the telematics load sensor readings, along with corresponding business rules, to determine carload status at a plant site location. This information is provided to the ERP system in preparation for car shipment. |
| 4 | Send Invoice Initiation | The application uses the telematics load sensor readings, along with corresponding business rules, to determine car unload or tapped status at a customer location. This information is fed to the ERP system and automatically initiates a customer invoice. |
| 5 | Create Demurrage Invoice | The application uses the telematics location/geo-fence readings, along with corresponding business rules, to determine the duration of idle times at customer locations. This information is to the ERP system to initiate a customer invoice for idle times over contractual limits. |
| 6 | Create FOB Invoice | The application uses the telematics location/geo-fence readings, along with corresponding business rules, to determine when a car enters a particular area of interest. This information is provided to the ERP system to initiate a FOB (Free on Board) invoice after crossing a geo-boundary. |
| 7 | Report on Customer Usage | Account Mangers and Customers define product usage metrics and the information that is tracked at a customer site. The application determines customer usage based on depletion of car inventory over time by using the load sensor readings and corresponding application business rules. Typically, this information is only available from the customer and is not available as a real-time reporting capability. |
| 8 | Provide Usage History | The application uses the telematics load sensor readings, along with corresponding application business rules, to determine customer usage history. This information is provided to the manufacturing enterprise systems as an input to the forecasting models. |
| 9 | Determine Geo-boundaries | A geo-boundary can be determined for existing, new, and modified customer deliveries automatically. The process for determining the geo-boundary can be automated by examining the ship-to address on critical delivery documentation, such as a BOL or invoice. Geo-boundaries can be manually modified as necessary. |

TABLE 2-continued

Applications of The Railcar Telematics System

| # | Name | Description |
|---|---|---|
| 10 | Send Route Transit Time | The application determines accurate route transit times. This information may be provided to enterprise systems to continually update route transit times with real-time data. |
| 11 | Maintain Key Performance Indicators | Business Managers have key metrics and targets that are tracked. They include: rail turns, on-time deliveries, inventory levels, on-site/in-transit car ratios, etc. The application stores the target values indicating whether users are properly managing their portion of the rail cycle. |
| 12 | Maintain Inventory Thresholds | Account Managers and Terminal Coordinators manage targeted product inventories at customer and terminal locations. The application stores minimum and maximum values as threshold indicators of business action. This information, coupled with the customer usage history, assists the management of inventory flow at the shipping terminals and customer facilities. |
| 13 | Maintain Alert Thresholds | The application stores pre-determined alert thresholds serving as indicators of business actions for each of the telemetry sensors deployed. Alert thresholds vary depending on business organization, fleet composition, product types, customer, manufacturing site, etc. The thresholds provide baseline alerts for particular roles and can be supplemented with customized alert thresholds. |
| 14 | Sensor Threshold Exceeded | The application notifies the Health & Safety system when an abnormal reading is detected from a railcar indicating a possible health or safety problem. |
| 15 | Geo-Lane Management | The application will allow the user to configure Geo-lanes, or Geo-paths, for railcars traveling along designated routes. Geo-lanes are composed of multiple sets of latitude/longitude coordinates along the rail routes. When a railcar carrying hazardous materials deviates from the designated route, an alert may be sent to a list of users. |

Figure 4:
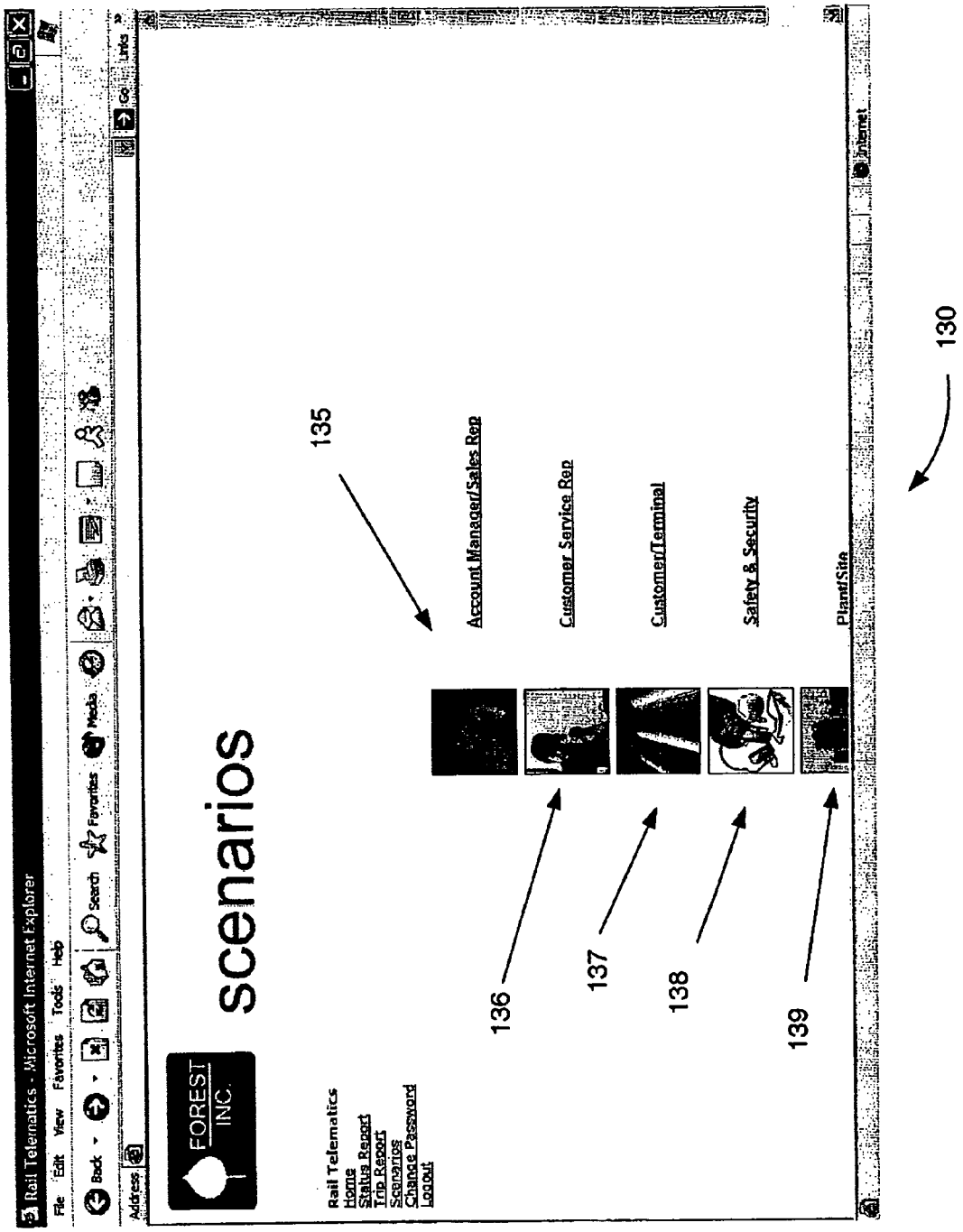
FIG. 4 is a web page view of a business user interface.

In one embodiment, the Railcar Telematics system may provide the business user 500 with a view for the status of the railcar 300 through the Web Site 130 in real-time. There are many different business users who will have a view of the Web Site 130 configured for the information that is relevant to the user's purpose and responsibilities. Options for the different scenarios of the views may be selected from a Web Site 130 as shown in FIG. 4. FIG. 4 shows a web page view that is visible when the user signs-in. The user will click on one of the icons or the linked user description to proceed to the appropriate view such as the "Account Manager/Sales Rep" icon 135. In another example, a customer will select the "Customer/Terminal" icon 137 and will have a view of the railcars and product status that are designated for the customer's use. That same customer will not be able to view the railcars 300 that are designated for another customer, especially one who may be a competitor.

In the "Customer Service Rep" view 136 or "Account Manager/Sales Rep" view 135, information for many customers would be relevant to the responsibility of that class. For example, an account manager might determine that a customer is running short of product and faces an imminent shutdown. The account manager has the option to divert a railcar 300 intended for delivery from one customer to another to make up the shortfall. This is information that may be restricted from the customers' views, and the Telematics application software will restrict such views to the appropriate user.

Figure 5:
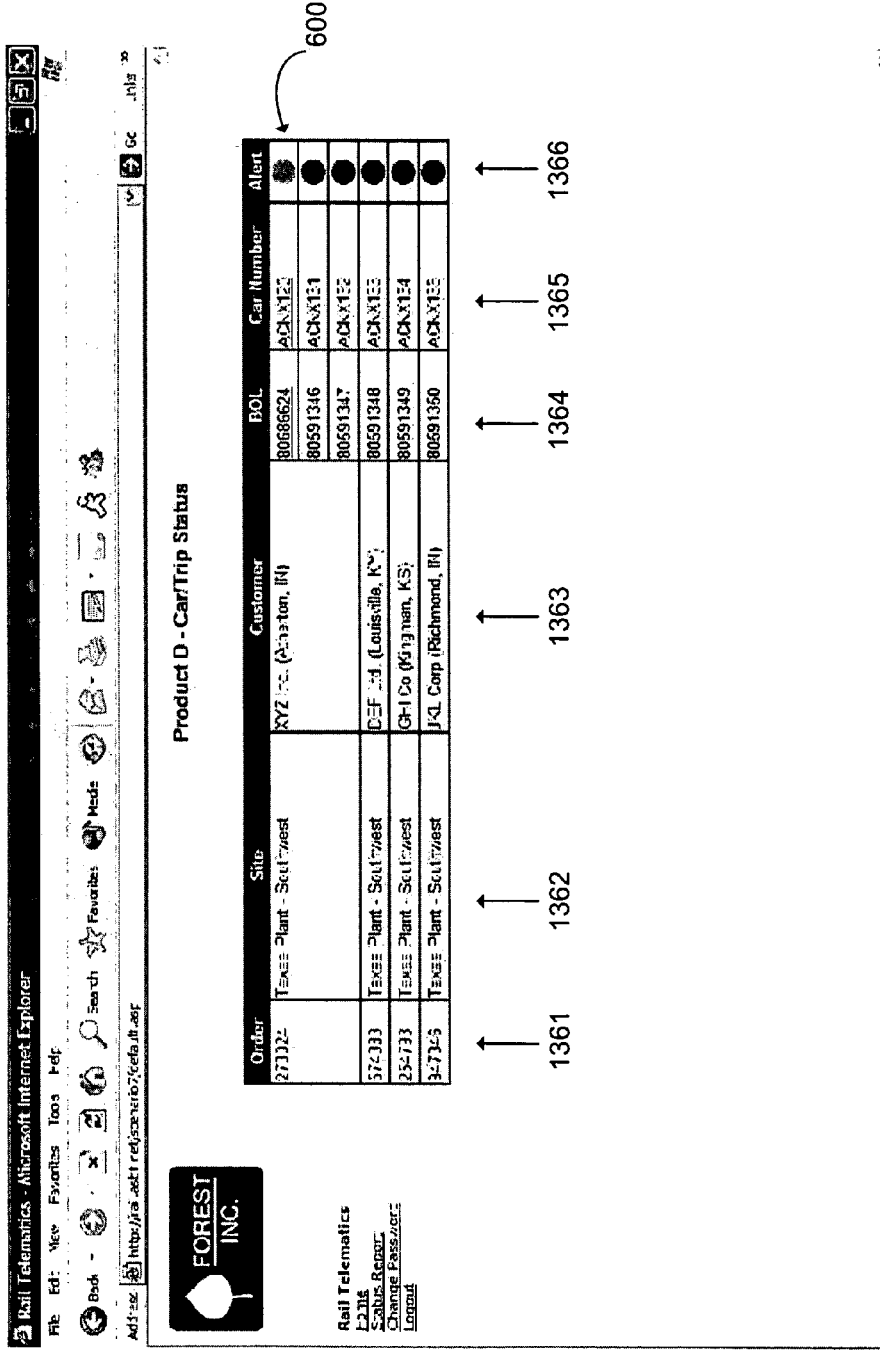
FIG. 5 is a web page summary view for Product Status.

When the customer service representative 136 selects a view, the representative may see the view 136 displaying relevant information for Product D as illustrated in FIG. 5. FIG. 5 is a spreadsheet that displays the order number 1361, the site 1362 where the product is produced, the customer 1363, the Bill of Lading 1364, the railcar 1365 associated with the Bill of Lading and the alert status column 1366 for each shipment regarding Product D. This view may display information regarding Product D for several customers, and as briefly described earlier, this web page would not be accessible for viewing by the customers.

Also in the Product D view 136, a proactive alert 600 is active for the railcar ACNX120. Displaying the alert in the view 136, is another method of informing the responsible business user that a proactive alert has been issued. Here, the alert 600 is for a railcar that is assigned to deliver Product D to company XYZ, Inc. In this embodiment, the business user may click on the alert to display or drill down to obtain a page with more detailed information regarding the alert.

Figure 6:
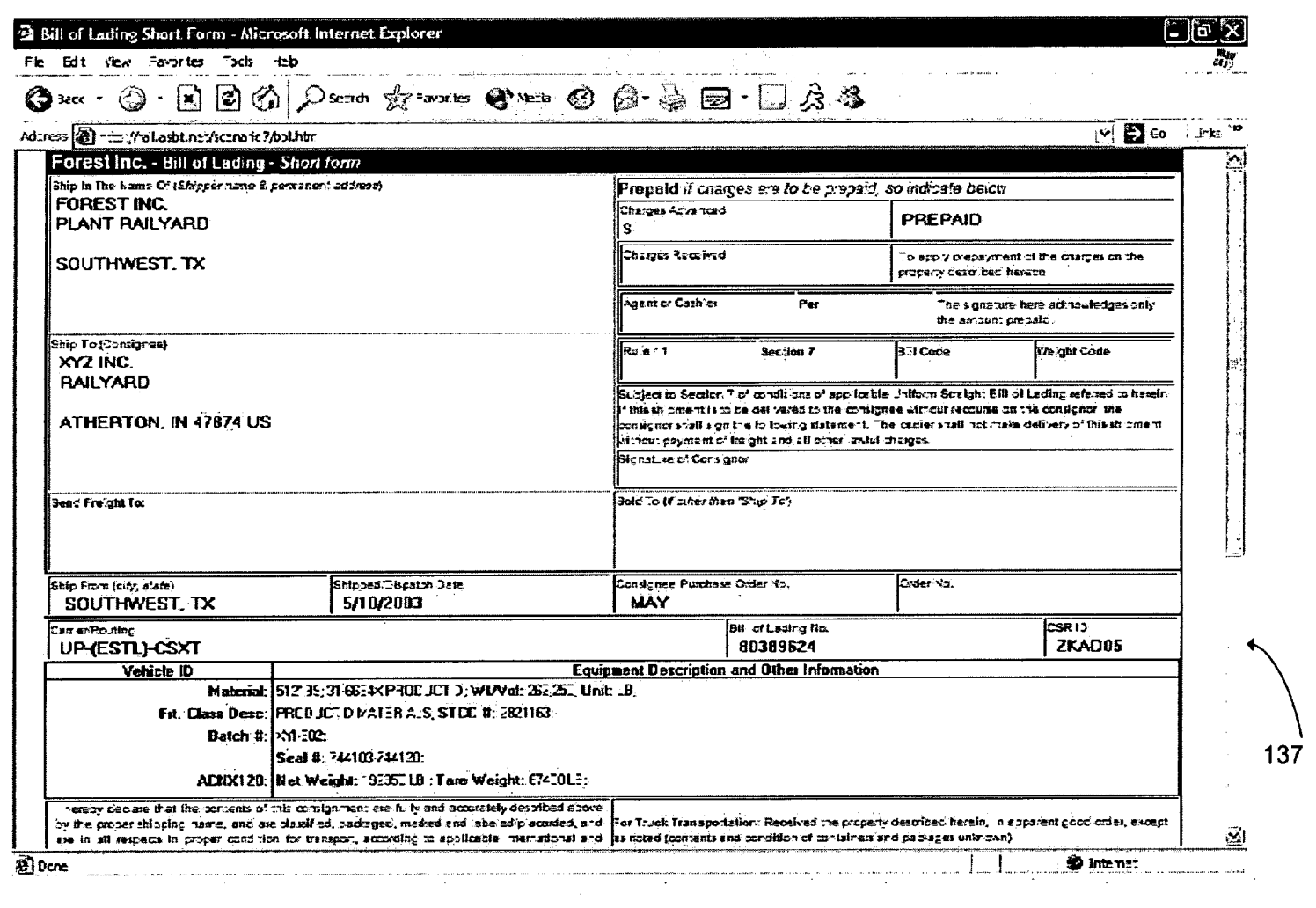

Alternatively, the customer service representative may click or drill down into information regarding a Bill of Lading 1364. FIG. 6 illustrates a view 137 of a typical Bill of Lading. The format for the Bill of Lading can be tailored to the manufacturer's needs or even the customer's needs if so requested.

Other views on the Web Site may be tailored to the requirements as well as the classification of business user. Table 3 presents a listing of some of the aggregations of possible views that may be assembled for the business user. An aggregation of a view may include information about a single railcar, a group of railcars associated with a product, a customer, or a plant manufacturer. This listing is by no means limiting in its scope of possibilities; on the contrary, one skilled in the art may find more features that could be added. As the amount of information transmitted by the Telematics sensor unit 310 of FIG. 2 increases, more categories of information can be added. Although the management of assets is the primary thrust, the management of material and more specifically the management of the inventory of material is the ultimate goal as the railcars do store material and product.

TABLE 3

Views Provided By The Railcar Telematic System

| | | |
|---|---|---|
| 1 | Railcar ETA View | When tracking railcars, the users may view an Estimated Time of Arrival (ETA) at either the customer destination or for the return of the empty railcar to the product manufacturer. This information is available from estimates based on historical calculations of the same trip, and are routinely updated if the railroad experiences delays. This information assists in making business decisions relative to customer service and asset utilization at the plant site. |
| 2 | Railcar Status Informational View | Through the personalized view of the application, users can see summary and detailed information about railcar status for their area of responsibility. This information is available in real-time, and includes relevant information for a particular railcar. This includes all sensor readings from the telematics unit, order information, delivery information, and derived information based on business rules. Railcar status can be viewed through an easy customized reporting tool, or as part of key alerts triggered by a user's role and preferences. |

TABLE 3-continued

Views Provided By The Railcar Telematic System

| | | |
|---|---|---|
| 3 | Site Railcar Statistics View | Through a different view of status information, users can access real-time views of all railcars on a site and their status. This view helps users manage both railcars and inventory at various locations on a particular site. |
| 4 | Inbound Railcar View | Users can access real-time views of all railcars inbound to the site and the status of the railcars. This view helps users with several responsibilities such as order demand planning, production planning, on site asset utilization efficiency/planning. |
| 5 | Railcar Idle-Time View | The application will display railcar idle times. Idle times within specific geo-boundaries such as customer location, terminal, rail sidings, plant and storage sites and other in-transit locations. The business rules may calculate the corresponding demurrage incurred at particular locations where idle times exceed the contractual limit. |
| 6 | Current Product Inventory View | Through role-based reporting views, users are able to see summary information about product inventory in railcars across their area of responsibility. This information is available in real-time and may provide an efficient method to view accurate inventory levels. |
| 7 | KPI View | Through role based reporting views, users are able to see summary information on how the railcar activities compare to a target KPI. This up-to-date information allows users to adjust their focus and/or take corrective actions. KPI's can include status, time duration, user defined values, and the number of railcars. |
| 8 | Fleet Performance Statistics View | Users see role-based summary information on overall fleet performance. This information serves as a key input into the fleet sizing model, providing trip "in-transit" and "hold" times, as well as the standard deviation. |
| 9 | Historical Site Status View | Site Logistics users can view critical information such as the number of railcars on site, and the railcar status and location. Users may compare how those statistics have fluctuated/changed over time. |
| 10 | Future Site Projections View | The application tracks current and historical site statistics, including the location and status of incoming railcars. With usage/historical information relative to the ratio of railcars inbound versus outbound, and real-time data on incoming railcars, the application can provide a projection of future site statistics. This information can be used as a planning tool for site management, as well as an indicator of railcar flow/turn issues. |
| 15 | View Home Page | The application will provide users with a specific home page customized to their role. |

Figure 7:
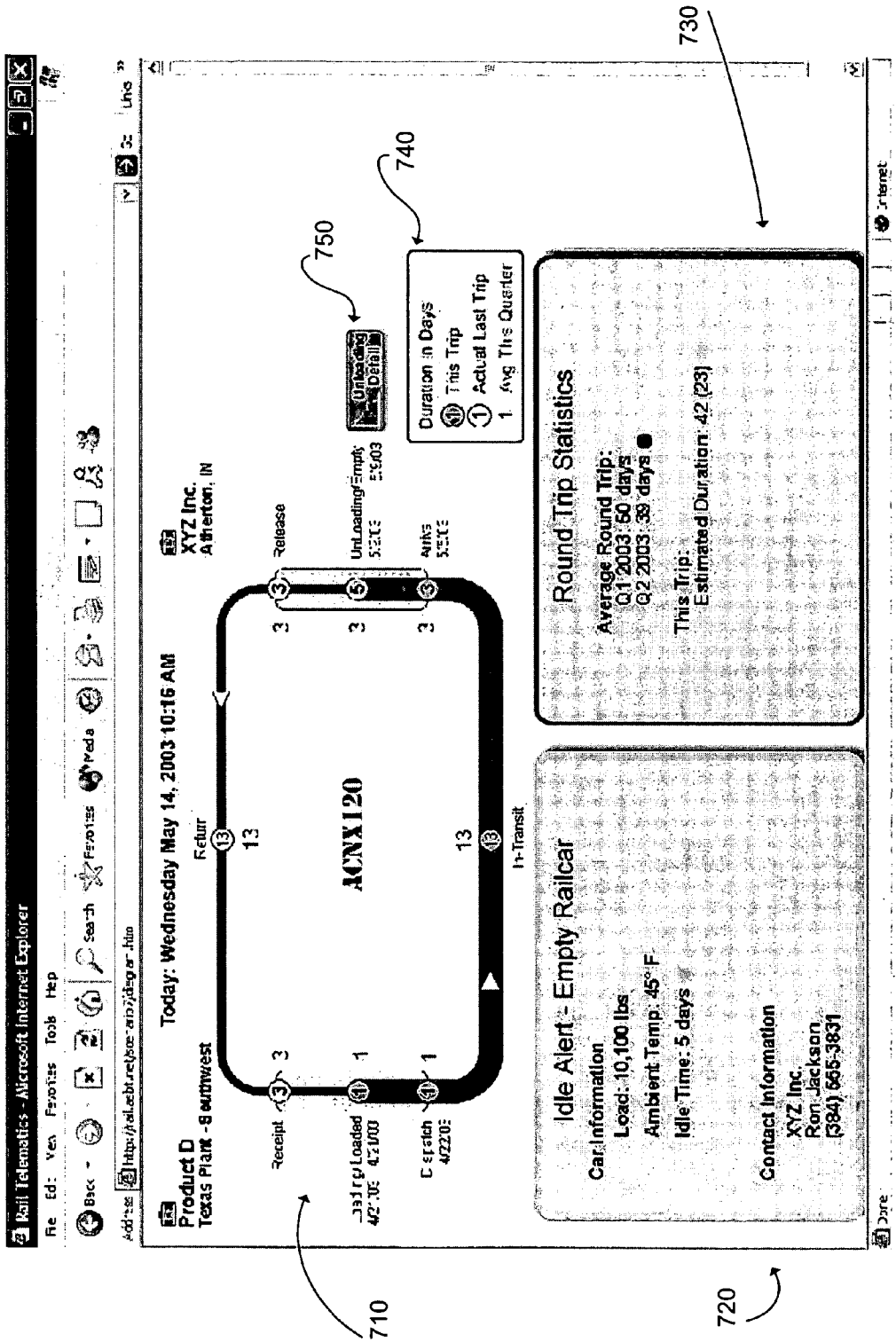
FIG. 7 is a web page view of a roundtrip cycle of a railcar.

FIG. 7 is a view of an embodiment of an alert page 700. It can be displayed when the customer service representative clicks on the alert as mentioned previously. The alert page 700 shows the roundtrip cycle of the railcar in the oval 710, an idle alert message 720 stating the reason for the alert, the round trip statistics 730 for this railcar, and the unloading detail 740. The roundtrip cycle 710 displays information regarding the unloading detail that includes the duration of the unloading in days. The round trip statistics 730 shows that the quarterly averages for the round trip for the last two quarters were 50 and 39 days, respectively. The estimated duration for this trip is 43 days with the actual number of days (in parenthesis), 23 days, that have elapsed since the current trip began. The unloading detail 740 shows the number of days that the unloading took for this trip and the average number of days for the quarter.

This view may be tailored to several cars, giving the appropriate details for each car and the status of each car and its position in the graphical representation. Further, a fleet may be represented in such a graph and the cars categorized for the product and the customer that receives the respective product. Such a display would show the position of the railcar in the graphical representation, its load and destination and the estimated time of arrival. It may be color-coded to further illustrate its status.

Figure 8:
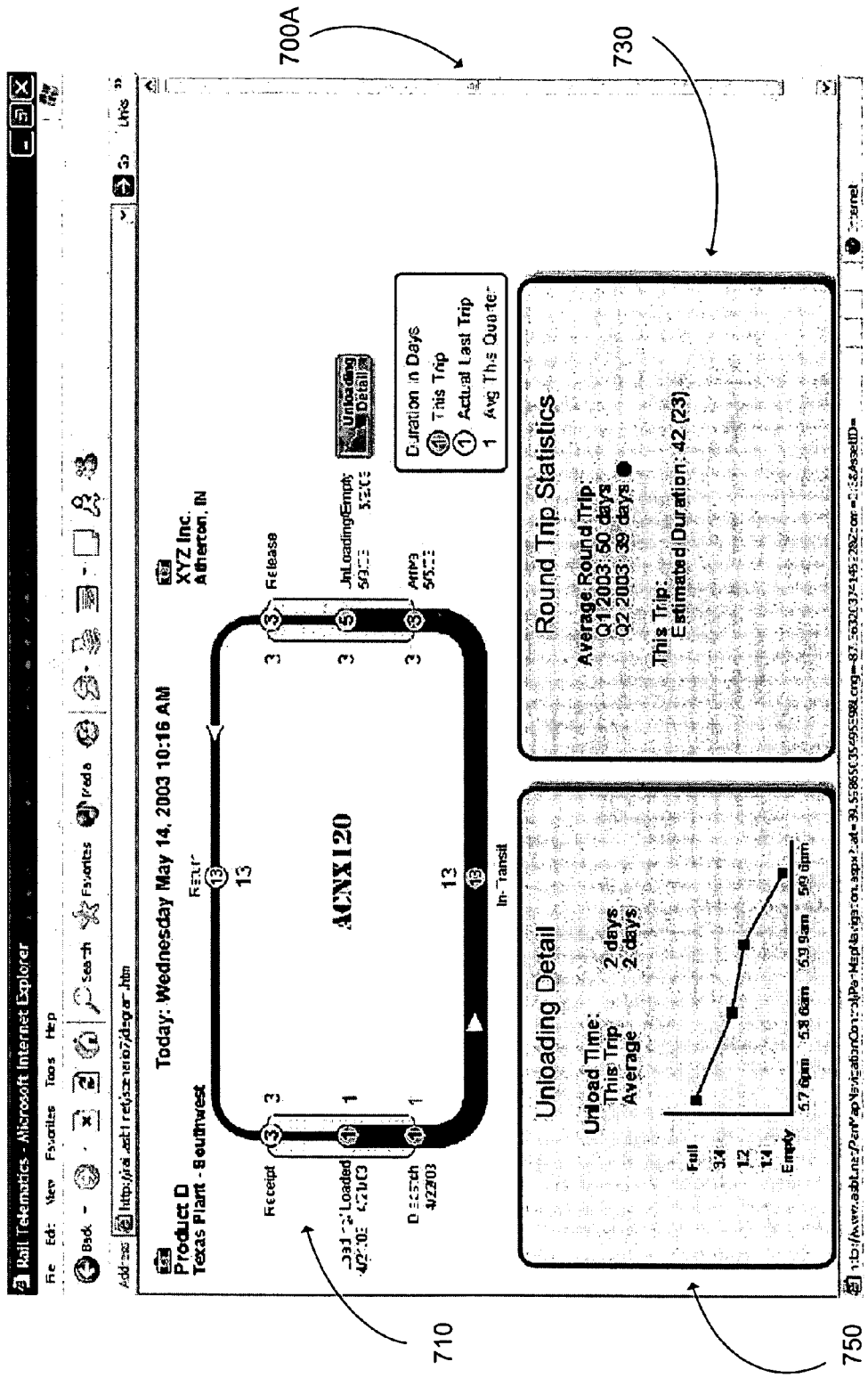
FIG. 8 is a web page view of a different roundtrip cycle of a railcar.

As FIG. 8 illustrates, the alert was issued because the railcar is idle 720 and it has been sitting empty for 5 days. In order to resolve the alert, contact information for the appropriate party has been provided. Rather than provide an alert to the customer service representative, the Railcar Telematics System 100 may provide the alert to the customer. Contacting the customer avoids the unnecessary step of contacting the customer service representative until the customer does not respond to the alert for a predetermined amount of time.

In the round trip cycle 710 portion of FIG. 7, the estimated time for the trip is listed in the inner radius of the oval. By adding the estimated time for each task in the roundtrip cycle, the estimated time for a trip cycle should take 40 days. The estimated duration is now 42 days. The round trip statistics 730 has been updated because of the 5 day idle time experienced by the railcar 300 after unloading. This idle time is of interest to the product manufacturer 139 and the customer service representative 136 and most likely the customer. As the railcar 300 sits, it accrues demurrage charges that will be applied to the customer. The idle time is time that a capital asset is not otherwise being employed for its intended purpose, thus driving up costs for the product manufacturer. To view more detailed information regarding the idle time, the user may drill down in the unloading detail 750.

FIG. 8 illustrates a typical Web Site view 700A that may be displayed when the business user drills down for more information regarding the unloading. This view 700A shows three major areas of information. The oval 710 shows the same round trip parameters as in FIG. 7 and the round trip statistics 730. The Unloading Detail 750 is a new feature in this view and provides the business user with information for the unloading process and how long the unloading process took. In this example, the railcar was tapped on May 7 at approximately 6 PM and the unloading was completed on May 9 at approximately 6 PM, making the unload time 2 days.

Figure 9:
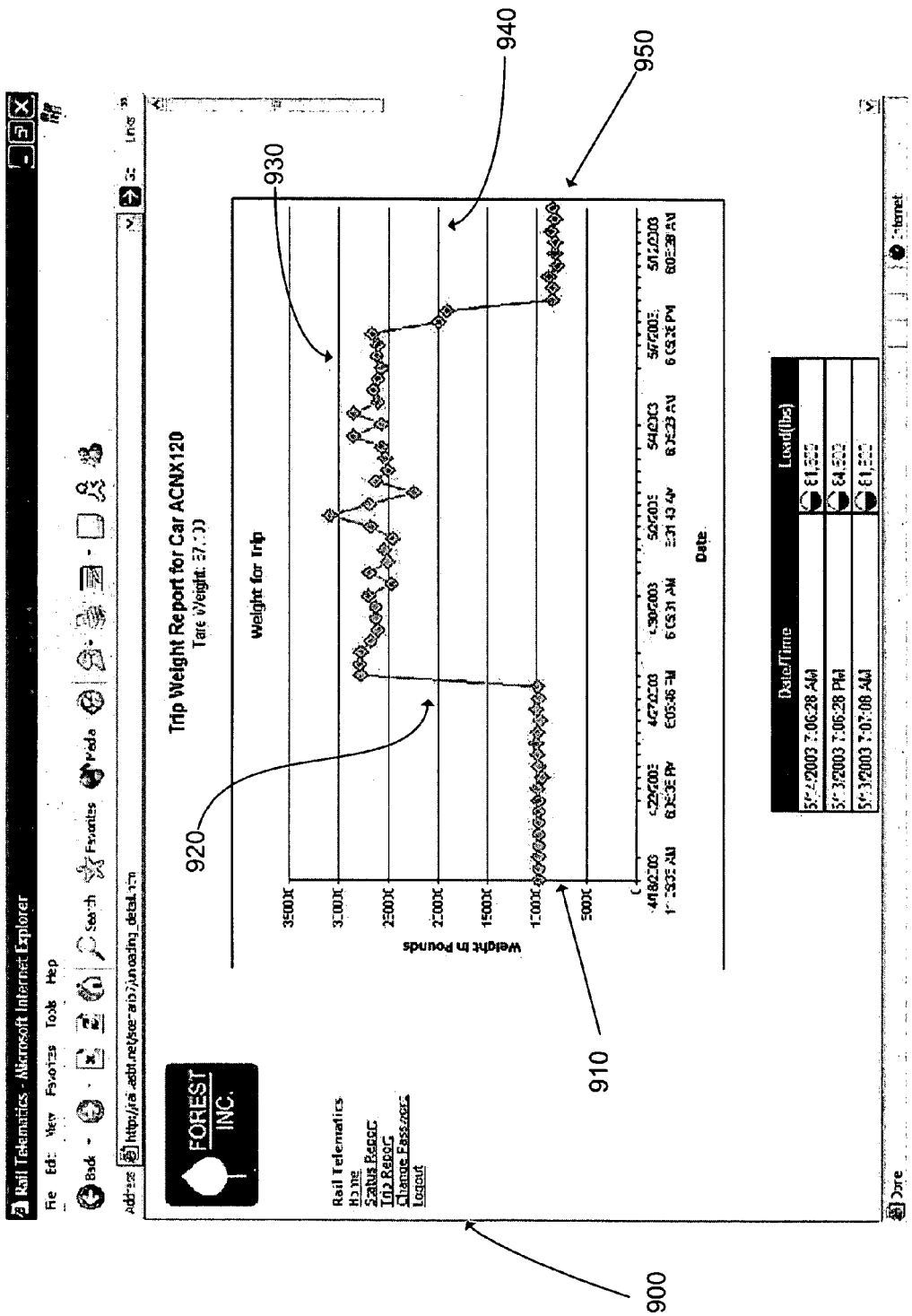
FIG. 9 is a web page view of a Weight Trip Report.

From the view in FIG. 8, the business user may drill down even further to obtain a Trip Weight Report 900 shown in FIG. 9. This weight report shows the weight of the railcar as it sat empty 910 before loading, the point where it was loaded 920, and the weight readings as the railcar traveled down the rail line 930 to the customer. The graph also shows the time the railcar was unloaded 940 at the customer site. By way of example, the report shows when the Telematics Sensing unit 310 on the railcar 300 sent two reports as the railcar 300 was unloading 940.

Figure 10:
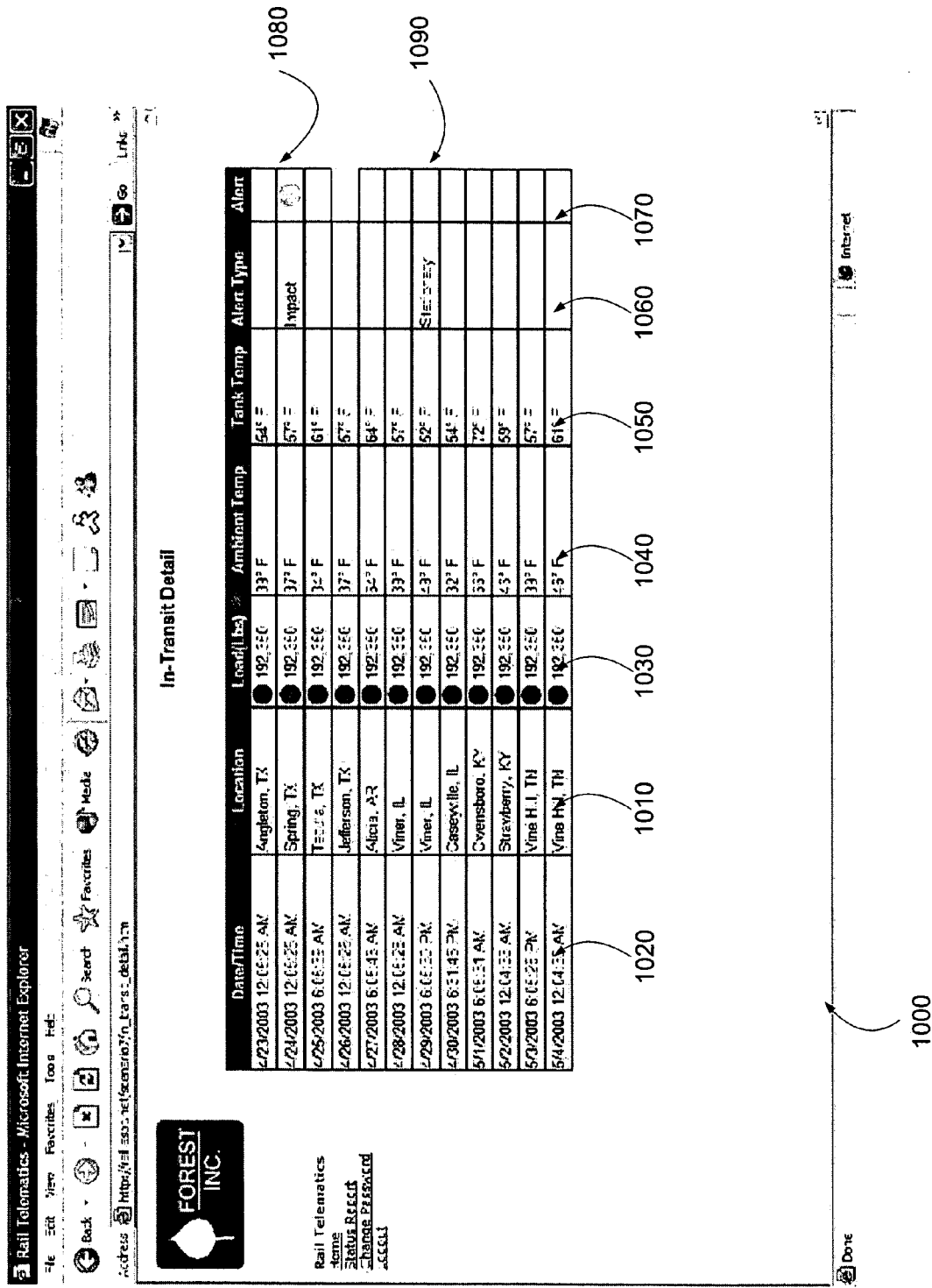
FIG. 10 is a web page view of an In-Transit Detail Report.

If the customer service representative desires detailed information about the trip, the representative alternatively may drill into the trip portion of the Web Site shown in FIG. 8 to obtain the spreadsheet view 1000 of FIG. 10. FIG. 10 is a view 1000 of a spreadsheet displaying the location 1010 of each of the RFID sensors and the time 1020 that the RFID tag attached to the railcar passed by the sensor. Also displayed in this view is the Load weight 1030, the ambient temperature 1040, the railcar temperature 1050, the type of alert 1060, and the alert status 1080.

The customer service representative may view aggregations of views, meaning the views may include the fleet, a set of railcars for one customer or just one individual railcar 300. The customer service representative may be able to view the hold patterns, the transit times, the loading and unloading times. In views that are tailored to a particular user, the user may be able to respond to alerts through the System, implementing a change or causing the System to implement a change to a metric of the business rules.

All of the status that the system monitors may be viewed in multiple detailed levels of data and information regarding the status of the railcar 300, the location of the railcar 300 and the status of the product. All of the proactive alerts and tasks may be displayed in the multiple levels of detail as well.

Figure 11:
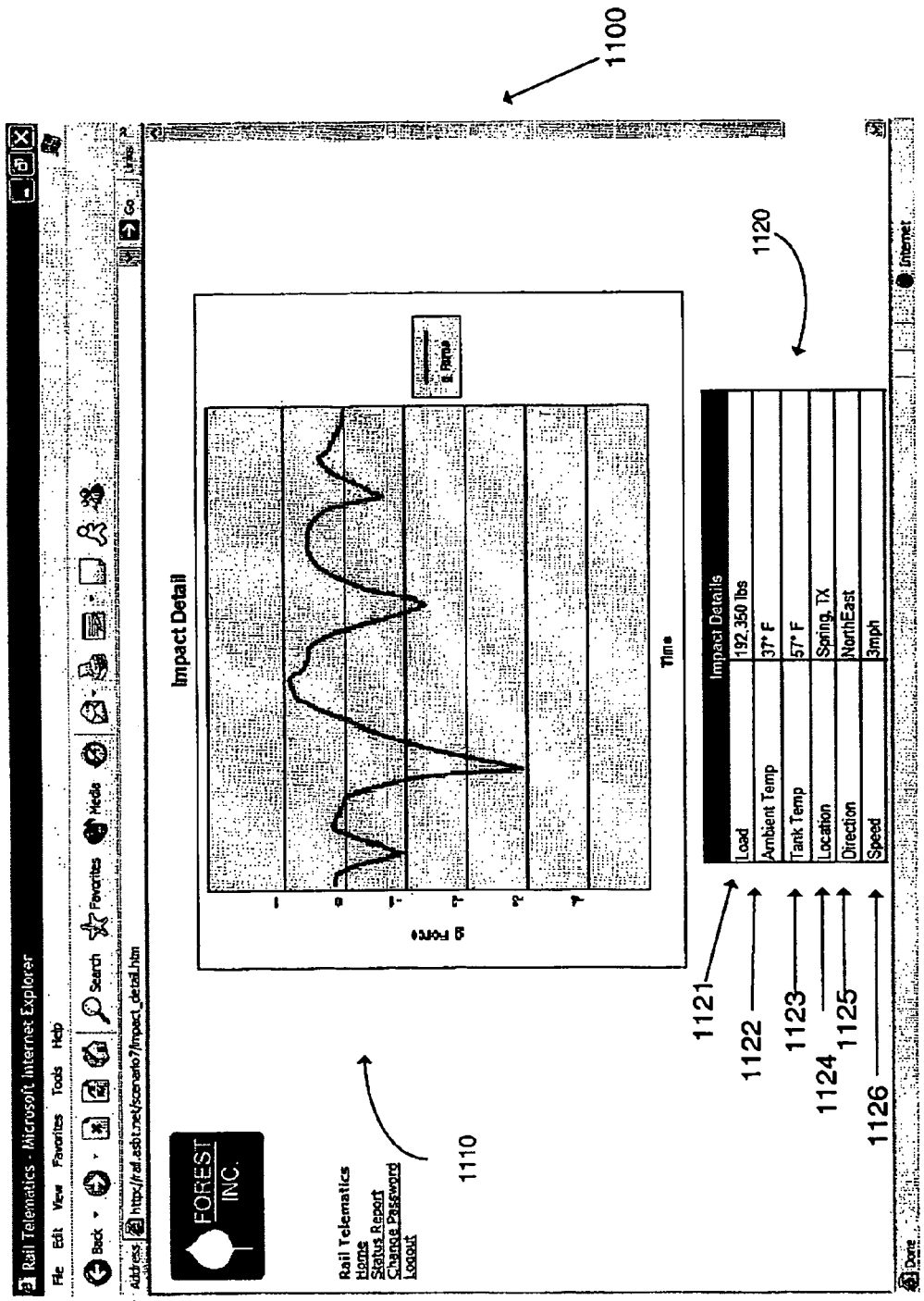
FIG. 11 is a web page view of an Impact Detail Report.

As an example, two alerts are shown in FIG. 10. The first alert is an impact alert 1080. The impact alert is sent in response to the railcar 300 sustaining a higher than usual impact. The impact may have occurred when the train was assembled. Sometimes these impacts damage the cars resulting in higher maintenance costs. In an effort to mitigate the costs of repair, the time, place and repetitious nature of these impacts are recorded for subsequent compensation and to reduce the freighting costs. An alert may be recorded by the Telematics Sensing unit 310 attached to the railcar 300 and sent at the earliest convenience, if not immediately upon impact. Alternatively, the railcar's location upon impact may be derived by the business alert engine 120 based on communication from the RFID sensors. The magnitude of the impact to the railcar may also be recorded and available to the business user on the Web Site 130. A view of an impact detail 1100 is shown in FIG. 11.

In the impact detail view 1100, a graph 1110 shows the magnitude and the direction of the impacts versus time. The view 1100 shows an Impact Detail table 1120 displaying the status of the railcar at the time of the impact. The table 1120 also lists the loaded weight 1121, the ambient temperature 1122, the railcar temperature 1123, the location 1124 of the railcar, the direction 1125 in which the car was positioned and the speed 1126 of the railcar at the time of impact.

In some instances the impact can result in a bad-ordered car. A bad-ordered car is a railcar 300, as determined by the railway, requiring repair before the railcar 300 can be used to further transport the product to the customer. A bad-ordered railcar may require that another fully loaded railcar be sent to the intended customer of the bad-ordered railcar. If the product is time-sensitive to degradation, it may mean that the replacement of the product on the bad-ordered railcar is necessary. This loss of product would be part of any damage assessment resulting from the impact and it may be tracked in the ERP System.

It is important to track the impact events as described above in order to place the actual costs on the responsible party. By tracking the time, date and location, the owner of the railcar may determine who had possession of the railcar 300 at the time of impact. Such damage will be assessed to the responsible party.

In one embodiment, the Railcar Telematics System may be capable of tracking impacts and monitoring seals attached to the hatches and valves. Emergency and safety personnel dispatched to the scene of the accident may obtain some information regarding the condition of the railcars and formulate a response scenario. Information transmitted from the Telematics Sensor unit 310 may provide information that the railcar 300 is not leaking because the railcar 300 weighs the same. The Telematics Sensor unit 310 may transmit that the impact experienced by the railcar 300 was not great enough. If the Railcar Telematics system 100 creates no proactive alerts for the railcar 300 after such an event, it is an indication that the railcar 300 may not have been involved. This is true where the user can send a status query to the railcar 300 and the railcar 300 replies. This information may help response personnel direct their efforts to the more critical aspects of the situation.

In another example, railcars transporting hazardous materials may be monitored for leaking valves or hatches. The hatches may have been opened or otherwise compromised. Compromised means that the government required safety seal on the hatch was broken. However, a seal on a valve or hatch does not have to be compromised in order for the railcar 300 to leak. A seam in the railcar may have split, leaking product. In such a case the weight of the railcar 300 will decrease over time.

A response to a proactive alert, where the seal indicates that the hatch or valve may be compromised, might be to stop the transport of the railcar 300 if the railcar 300 is traveling into a populated area. Alternatively, if the railcar 300 is near a population center, a response to a proactive alert might be the removal of the railcar 300 from the populated area. In a heightened state of national security, railcars 300 carrying hazardous materials may be tracked and under certain heightened restrictions may be located and directed to a common area where they may be secured.

Many of the web page views that have been discussed are generally available through a computer terminal screen whether the computer is a desktop or laptop, however the views are not necessarily limited to these devices. Any device capable of viewing a web page and having access to the Internet may be used download the web page. Such devices may include PDAs, television screens and even cell phones that have web capabilities.

Figure 12:
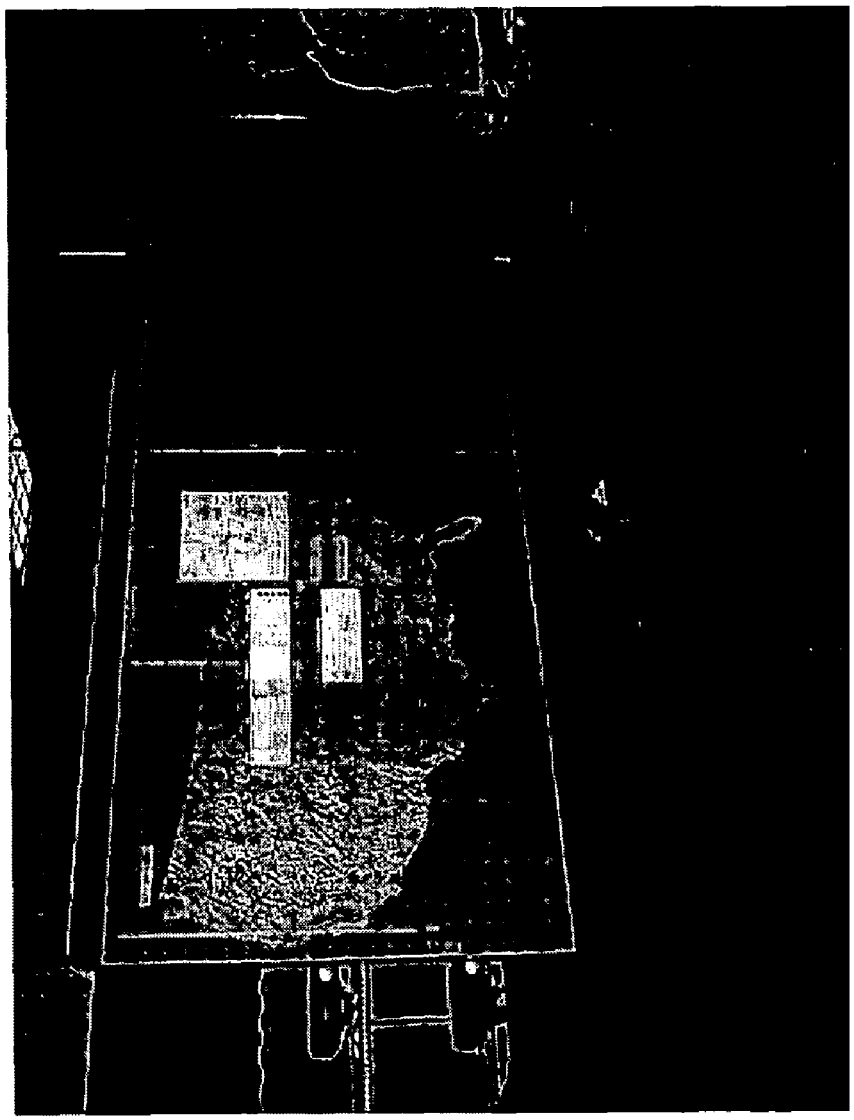
FIG. 12 is a Large Screened User Interface.

The views described above may even be accessible and presented in a Strategic Decision Center that allows for a large viewing screen which permits interaction between the user and the Railcar Telematics System. Such a screen is shown in FIG. 12. The displayed view 1200 has a map overlay of the railcars that make up a fleet for a product manufacturer. A feature of using a large screen 1300 is that the screen may provide the user with a "fleet wide" graphical view of all the railcars in the system at once. Although not visible, the railcars may be associated with a color-code to gauge the status of the individual cars.

Figure 13:
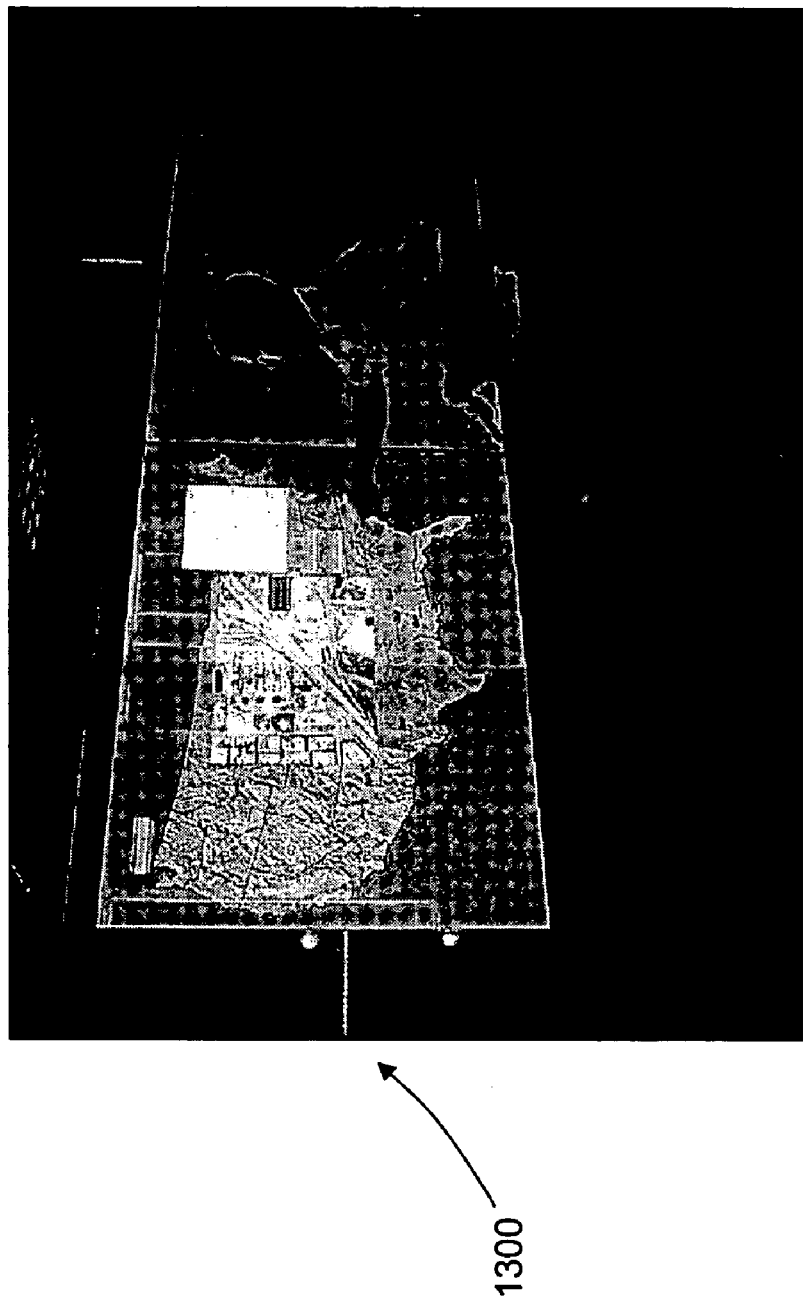
FIG. 13 is a Large Screen User Interface displaying a satellite view.
Figure 14:
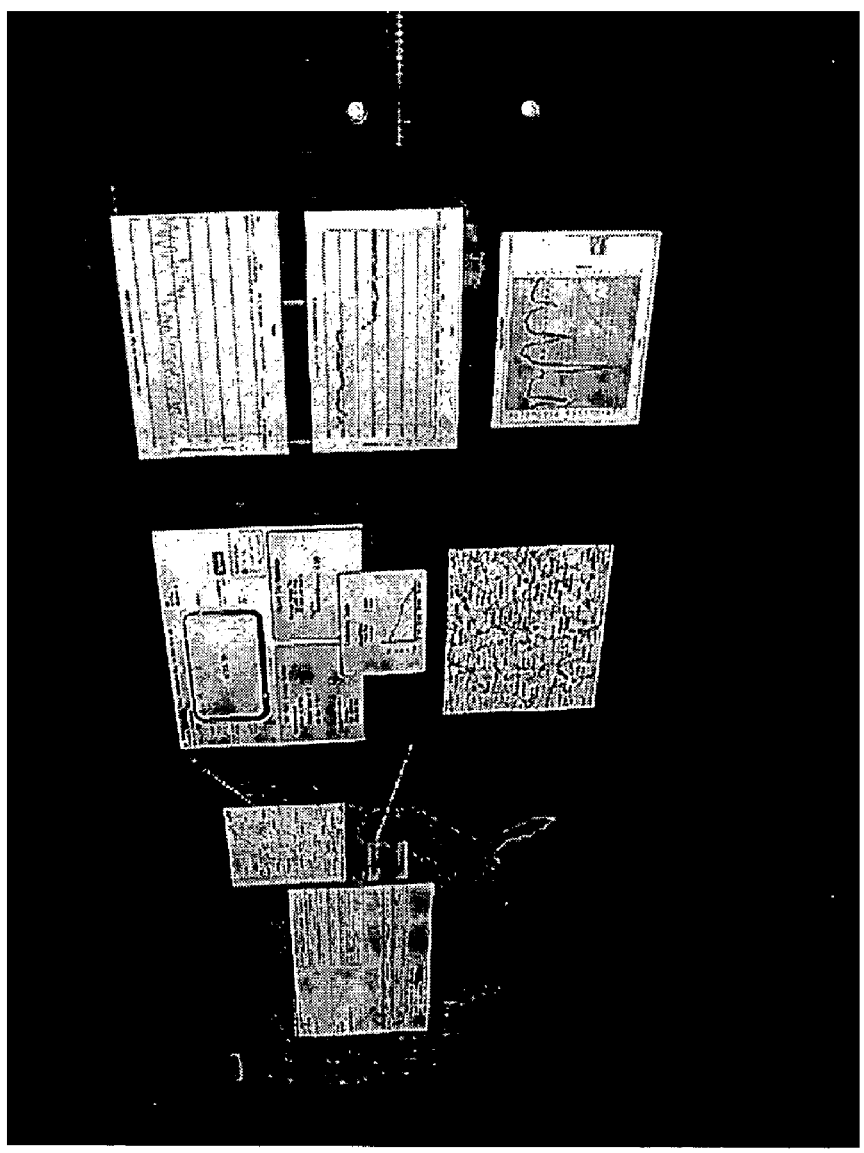
FIG. 14 is a Large Screen User Interface displaying multiple web page views.

The users, by touching the screen, may interact with the display and when "drilling down" into a web page may be able to place a view of the new web page or view alongside the previous view. FIG. 13 shows a view 1300 of the screen where a satellite view is superimposed over the map of the United States. As more information is required, the user may be able to display any of the views, which were described earlier, so that the multiple web pages are displayed on the screen at once. Such a view 1400 of the embodiment is shown in FIG. 14.

In one implementation, the user may be able to stream real-time video alongside the data on the touch screen. The real-time video may originate from a security camera in a rail yard, a customer site or from the product manufacturer's facility. Another feature of the screen is that a video conference can be staged and the users at both locations may interactively participate by manipulating the data while discussing strategy and tactics. As the data is spread out across the screen, different users may bring up views of various screens that have linked data between the screens. The multiple screens may provide the opportunity to discuss several different scenarios in a conference room setting.

It is therefore intended that the foregoing detailed description be regarded as illustrative rather than limiting, and that it be understood that it is the following claims, including all equivalents, that are intended to define the spirit and scope of this invention.

We claim:

1. A method for the management of railcar assets comprising:

receiving data regarding a time and location of a railcar and a status of a product on the railcar;

storing the data in a railcar database;

comparing the status of the product on the railcar to a status alert threshold;

issuing a status alert when the comparison reveals that the status of the product on the railcar meets the status alert threshold;

monitoring status alerts issued based on the status of the product on the railcar meeting the status alert threshold, including instances where a status alert is resolved before anyone takes action;

based on the monitoring, determining a value of repetitiveness of status alerts issued based on the status of the product on the railcar meeting the status alert threshold;

comparing the value of repetitiveness of status alerts issued based on the status of the product on the railcar meeting the status alert threshold to a repetitiveness threshold; and when the comparison reveals that the value of repetitiveness meets the repetitiveness threshold, issuing a proactive alert.

2. The method of claim 1, further comprising monitoring historical data that includes a round trip time of the railcar, a time for loading, a transit time to the customer site, a time for unloading the railcar, and a time to return to a product manufacturer.

3. The method of claim 1, further comprising monitoring historical data that includes status information.

4. The method of claim 1:

wherein receiving data regarding a time and location of a railcar and a status of a product on the railcar comprises receiving data regarding a temperature of the product on the railcar;

wherein comparing the status of the product on the railcar to a status alert threshold comprises comparing the temperature of the product on the railcar to a temperature alert threshold;

wherein issuing a status alert when the comparison reveals that the status of the product on the railcar meets the status alert threshold comprises issuing a status alert when the comparison reveals that the temperature of the product on the railcar is above the temperature alert threshold;

wherein monitoring status alerts issued based on the status of the product on the railcar meeting the status alert threshold, including instances where a status alert is resolved before anyone takes action comprises monitoring status alerts issued based on the temperature of the product on the railcar meeting the temperature alert threshold, including instances where the temperature drops to resolve the status alert before anyone takes action;

wherein determining a value of repetitiveness of status alerts issued based on the status of the product on the railcar meeting the status alert threshold comprises determining a value of repetitiveness of status alerts issued based on the temperature of the product on the railcar meeting the status alert threshold; and wherein comparing the value of repetitiveness of status alerts issued based on the status of the product on the railcar meeting the temperature alert threshold to a repetitiveness threshold comprises comparing the value of repetitiveness of status alerts issued based on the temperature of the product on the railcar meeting the temperature alert threshold to a repetitiveness threshold.

5. The method of claim 1, further comprising monitoring for responses to the proactive alert and escalating the proactive alert based on a determination of a lack of acknowledgement or resolution of the proactive alert.

6. The method of claim 1, wherein issuing the proactive alert comprises sending the proactive alert to at least one of a shipper, a customer, and a product manufacturer, further comprising reassigning responsibilities for the proactive alert to another user.

7. The method of claim 1, further comprising changing the repetitiveness threshold to reduce a number of proactive alerts issued for repetitive status alerts.

8. A railcar asset management system comprising:
a communication system interface that receives data regarding a time and location of a railcar and a status of a product on the railcar;
a database that stores the data regarding the time and location of the railcar and the status of the product on the railcar received from the communication system interface;
a rules database including a rule defining a status alert threshold and a status alert and a rule defining a repetitiveness threshold and a proactive alert;
a data processor in communication with the communication system interface and the databases, the data processor operable to compare the status of the product on the railcar to the status alert threshold, issue the status alert when the comparison reveals that the status of the product on the railcar meets the status alert threshold, monitor status alerts issued based on the status of the product on the railcar meeting the status alert threshold, including instances where a status alert is resolved before anyone takes action, determine a value of repetitiveness of status alerts issued based on the status of the product on the railcar meeting the status alert threshold, compare the value of repetitiveness of status alerts issued based on the status of the product on the railcar meeting the status alert threshold to a repetitiveness threshold, and, when the comparison reveals that the value of repetitiveness meets the repetitiveness threshold, issue the proactive alert; and
an alert interface in communication with the data processor that communicates the proactive alert outside the railcar asset management system.

9. The railcar asset management system of claim 8, wherein the data processor is operable to monitor historical data that includes a round trip time of the railcar, a time for loading, a transit time to the customer site, a time for unloading the railcar, and a time to return to a product manufacturer.

10. The railcar asset management system of claim 8, wherein the data processor is operable to monitor historical data that includes status information.

11. The railcar asset management system of claim 8:
wherein the communication system interface receives data regarding a temperature of the product on the railcar;
wherein the rules database includes a rule defining a temperature alert threshold and a status alert; and
wherein the data processor is operable to compare the temperature of the product on the railcar to the temperature alert threshold, issue the status alert when the comparison reveals that the temperature of the product on the railcar meets the temperature alert threshold, monitor status alerts issued based on the temperature of the product on the railcar meeting the temperature alert threshold, including instances where the temperature drops to resolve the status alert before anyone takes action, determine a value of repetitiveness of status alerts issued based on the temperature of the product on the railcar meeting the temperature alert threshold, and compare the value of repetitiveness of status alerts issued based on the temperature of the product on the railcar meeting the status alert threshold to a repetitiveness threshold.

12. The railcar asset management system of claim 8, wherein the data processor is operable to monitor for responses to the proactive alert and escalate the proactive alert based on a determination of a lack of acknowledgement or resolution of the proactive alert.

13. The railcar asset management system of claim 8, wherein the data processor is operable to send the proactive alert to at least one of a shipper, a customer, and a product manufacturer and reassign responsibilities for the proactive alert to another user.

14. The railcar asset management system of claim 8, wherein the data processor is operable to change the repetitiveness threshold to reduce a number of proactive alerts issued for repetitive status alerts.

15. A non-transitory computer-readable storage medium encoded with executable instructions that, when executed by at least one processor, cause the at least one processor to perform operations comprising:
receiving data regarding a time and location of a railcar and a status of a product on the railcar;
storing the data in a railcar database;
comparing the status of the product on the railcar to a status alert threshold;
issuing a status alert when the comparison reveals that the status of the product on the railcar meets the status alert threshold;
monitoring status alerts issued based on the status of the product on the railcar meeting the status alert threshold, including instances where a status alert is resolved before anyone takes action;
based on the monitoring, determining a value of repetitiveness of status alerts issued based on the status of the product on the railcar meeting the status alert threshold;
comparing the value of repetitiveness of status alerts issued based on the status of the product on the railcar meeting the status alert threshold to a repetitiveness threshold; and
when the comparison reveals that the value of repetitiveness meets the repetitiveness threshold, issuing a proactive alert.

16. The computer-readable storage medium of claim 15, further comprising monitoring historical data that includes a round trip time of the railcar, a time for loading, a transit time to the customer site, a time for unloading the railcar, and a time to return to a product manufacturer.

17. The computer-readable storage medium of claim 15, further comprising monitoring historical data that includes status information.

18. The computer-readable storage medium of claim 15:
wherein receiving data regarding a time and location of a railcar and a status of a product on the railcar comprises receiving data regarding a temperature of the product on the railcar;
wherein comparing the status of the product on the railcar to a status alert threshold comprises comparing the temperature of the product on the railcar to a temperature alert threshold;

wherein issuing a status alert when the comparison reveals that the status of the product on the railcar meets the status alert threshold comprises issuing a status alert when the comparison reveals that the temperature of the product on the railcar is above the temperature alert threshold;

wherein monitoring status alerts issued based on the status of the product on the railcar meeting the status alert threshold, including instances where a status alert is resolved before anyone takes action comprises monitoring status alerts issued based on the temperature of the product on the railcar meeting the temperature alert threshold, including instances where the temperature drops to resolve the status alert before anyone takes action;

wherein determining a value of repetitiveness of status alerts issued based on the status of the product on the railcar meeting the status alert threshold comprises determining a value of repetitiveness of status alerts issued based on the temperature of the product on the railcar meeting the status alert threshold; and wherein comparing the value of repetitiveness of status alerts issued based on the status of the product on the railcar meeting the temperature alert threshold to a repetitiveness threshold comprises comparing the value of repetitiveness of status alerts issued based on the temperature of the product on the railcar meeting the temperature alert threshold to a repetitiveness threshold.

19. The computer-readable storage medium of claim 15, wherein the operations further comprise monitoring for responses to the proactive alert and escalating the proactive alert based on a determination of a lack of acknowledgement or resolution of the proactive alert.

20. The computer-readable storage medium of claim 15, wherein issuing the proactive alert comprises sending the proactive alert to at least one of a shipper, a customer, and a product manufacturer, and the operations further comprise reassigning responsibilities for the proactive alert to another user.

* * * * *

UNITED STATES PATENT AND TRADEMARK OFFICE
CERTIFICATE OF CORRECTION

| | | |
|---|---|---|
| PATENT NO. | : 8,045,962 B2 | Page 1 of 1 |
| APPLICATION NO. | : 11/208039 | |
| DATED | : October 25, 2011 | |
| INVENTOR(S) | : Schullian et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1832 days.

Signed and Sealed this
Thirteenth Day of March, 2012

David J. Kappos
*Director of the United States Patent and Trademark Office*